US006817230B2

United States Patent
James et al.

(10) Patent No.: US 6,817,230 B2
(45) Date of Patent: Nov. 16, 2004

(54) SYSTEMS AND METHODS FOR DETERMINING THE ABSORPTION AND SPECIFIC GRAVITY PROPERTIES OF COMPACTED AND LOOSE MATERIAL INCLUDING FINE AND COARSE AGGREGATES

(75) Inventors: Lawrence James, Raleigh, NC (US); Ali Regimand, Raleigh, NC (US)

(73) Assignee: InstroTek, Inc., Raleigh, NC (US)

( * ) Notice: Subject to any disclaimer, the term of this patent is extended or adjusted under 35 U.S.C. 154(b) by 0 days.

(21) Appl. No.: 10/462,499

(22) Filed: Jun. 16, 2003

(65) Prior Publication Data

US 2003/0213290 A1 Nov. 20, 2003

Related U.S. Application Data

(62) Division of application No. 09/976,530, filed on Oct. 11, 2001, now Pat. No. 6,615,643.
(60) Provisional application No. 60/240,563, filed on Oct. 13, 2000.

(51) Int. Cl.$^7$ .............................. G01N 5/02; G01N 9/10
(52) U.S. Cl. .............................. 73/73; 73/32 R; 73/437
(58) Field of Search ............................ 73/30.01, 32 R, 73/73, 433, 437

(56) References Cited

U.S. PATENT DOCUMENTS 4,083,228 A   4/1978   Turner et al. ............... 73/32 R (List continued on next page.)

FOREIGN PATENT DOCUMENTS

DE          2004530 A   8/1971

(List continued on next page.)

OTHER PUBLICATIONS

ASTM D 6752, Bulk Specific Gravity and Density of Compacted Bituminous Mixtures Using Automatic VAcuum Sealing Method, (no date).*

(List continued on next page.)

Primary Examiner—C D Garber
(74) Attorney, Agent, or Firm—Myers Bigel Sibley & Sajovec PA

(57) ABSTRACT

Methods, systems, and computer program products determine absorption, specific gravity, and/or porosity of construction materials undergoing analysis corresponding to different measurements of material samples divided from a "parent" construction material sample. Dry and wet weights of the samples are obtained under different conditions.

In certain embodiments, the material sample is an aggregate that is held in liquid in a volumetric container and the container with the liquid and aggregate is weighed. Another weight of a second sample can be obtained. The second sample is encased in an evacuated vacuum-sealed bag that is opened while immersed in a liquid bath, at which time the weight can be obtained. The weight data can be used to calculate the parameter of interest.

Other methods obtain one wet weight of the sample when it is positioned into the liquid bath at atmospheric pressure and the other weight is obtained when the sample is first held in an evacuated state in a sealed (compressible) bag is opened in the liquid bath. The weights can be used to determine the two densities.

Other methods employ evacuating a chamber holding a quantity of material sample under water in the container or subcontainer and obtaining weights of the sample under several conditions. Another method increases the pressure in the chamber and obtains weights of the sample under various conditions. Each of the methods determine the material property based on the measured weights. Related devices are also described.

17 Claims, 18 Drawing Sheets

U.S. PATENT DOCUMENTS

| | | | | |
|---|---|---|---|---|
| 4,383,864 A | * | 5/1983 | Trujillo | 106/281.1 |
| 5,760,293 A | | 6/1998 | Orr et al. | 73/32 R |
| 6,379,031 B1 | * | 4/2002 | Weingart et al. | 366/8 |
| 6,486,475 B1 | * | 11/2002 | Earle et al. | 250/341.8 |

FOREIGN PATENT DOCUMENTS

| | | | | |
|---|---|---|---|---|
| EP | 0936451 A1 | | 8/1999 | |
| JP | 62269040 A | | 5/1988 | |
| JP | 08304257 A | * | 11/1996 | G01N/9/02 |
| JP | 10010032 A | | 1/1998 | |
| WO | WO01/01108 | | 1/2001 | |

OTHER PUBLICATIONS

U.S. patent application Ser. No. 09/580,792, Regimand et al., filed May 30, 2000.

U.S. patent application Ser. No. 10/196,650, Regimand et al., filed Jul. 16, 2002.

Birello et al., "Advance in desity measurements by means of an automatic hydrostatic weighing system of 100 g capacity," Measurement, vol. 7, No. 4, pp. 157–162 (Oct.–Dec. 1989).

Dept. of Defense, "Standard Test Method for Bulk Specific Gravity and Density of Compacted Bituminous Mixtures Using Paraffin–Coated Specimens," ASTM Standards, Designation: D1188, pp. 118–120 (Oct. 1996).

Dept. of Defense, "Standard Test Method for Bulk Specific Gravity and Density of Non–Absorptive Compacted Bituminous Mixtures." ASTM Standards, Designation: D2726, pp. 242–244 (Oct. 1996).

Dept. of Defense, "Standard Test Method for Theoretical Maximum Specific Gravity and Density of Bituminous Paving Mixtures," ASTM Standards, Designation: D2041, pp. 176–182 (Dec. 1995).

Stephens, "Bituminous Mix Density by Coated Specimen," Project No. 67–5, Connecticut Dept. of Transportation (Jan. 1973).

Wolf, B., "Application of hydrostatic weighing to density determination of tiny porous samples," Rev. Sci. Instrum, vol. 66 (3), pp. 2578–2581 (Mar. 1995).

* cited by examiner

Worksheet for determination of % Absorption and gravity of aggregates

| 1 Weight of Aggregate In Unsealed bag | 2 Bag Wt. | 3 Weight of Aggregate and Unsealed bag in Water | 4 Weight of Aggregate In Sealed Bag | 5 Bag Wt. | 6 Weight of Sealed Bag and Aggregate opened Under Water | 7 ρ(U) | 8 ρ(V) | 9 Abs% +.35% correction | 10 C mass of saturated sample in water | 11 B mass of SSD sample in air | 12 Bsg | 13 Bsg SSD |
|---|---|---|---|---|---|---|---|---|---|---|---|---|
| 1011.1 | 21.1 | 610.6 | 1013.5 | 21.1 | 629.0 | 2.541 | 2.654 | 2.02 | 631.6 | 1034.0 | 2.519 | 2.570 |
| 1011.1 | 21.1 | 610.6 | 1001.7 | 21.1 | 621.7 | 2.541 | 2.654 | 2.03 | 624.3 | 1022.0 | 2.519 | 2.570 |
| 1011.1 | 21.1 | 610.6 | 1003.0 | 21.1 | 622.9 | 2.541 | 2.657 | 2.07 | 625.5 | 1023.7 | 2.519 | 2.571 |
| 1018.2 | 21.4 | 618.2 | 1013.5 | 21.1 | 629.0 | 2.552 | 2.654 | 1.69 | 631.6 | 1030.7 | 2.539 | 2.583 |
| 1018.2 | 21.4 | 618.2 | 1001.7 | 21.1 | 621.7 | 2.562 | 2.654 | 1.70 | 624.3 | 1018.7 | 2.539 | 2.583 |
| 1018.2 | 21.4 | 618.2 | 1003.0 | 21.1 | 622.9 | 2.562 | 2.657 | 1.74 | 625.5 | 1020.4 | 2.539 | 2.584 |
| 1003.1 | 21.4 | 608.2 | 1013.5 | 21.1 | 629.0 | 2.557 | 2.654 | 1.77 | 631.6 | 1031.5 | 2.534 | 2.579 |
| 1003.1 | 21.4 | 608.2 | 1001.7 | 21.1 | 621.7 | 2.557 | 2.654 | 1.78 | 624.3 | 1019.5 | 2.534 | 2.579 |
| 1003.1 | 21.4 | 608.2 | 1003.0 | 21.1 | 622.9 | 2.557 | 2.657 | 1.82 | 625.5 | 1021.2 | 2.534 | 2.580 |

$$\rho_U = \frac{Col(1)}{Col(1)+Col(2)-Col(3)-\frac{Col(2)}{0.891}}$$

$$\rho_V = \frac{Col(4)}{Col(4)+Col(5)-Col(6)-\frac{Col(5)}{0.891}}$$

FIGURE 10A

Aggregate Worksheet

Weight of Container and Lid filled with water: _____  1 _____  2 _____  3 _____ Avg _____

| Sample Number | A Dry Sample A Weight(g) | B Sample A Weight in Container Filled With Water(g) | C Bag Weight (g) | D Dry Sample B Weight(g) | E Weight of Sealed Sample B Opened in Water(g) |
|---|---|---|---|---|---|
| | | | | | |
| | | | | | |
| | | | | | |
| | | | | | |
| | | | | | |
| | | | | | |
| | | | | | |
| | | | | | |
| | | | | | |
| | | | | | |

FIGURE 10B

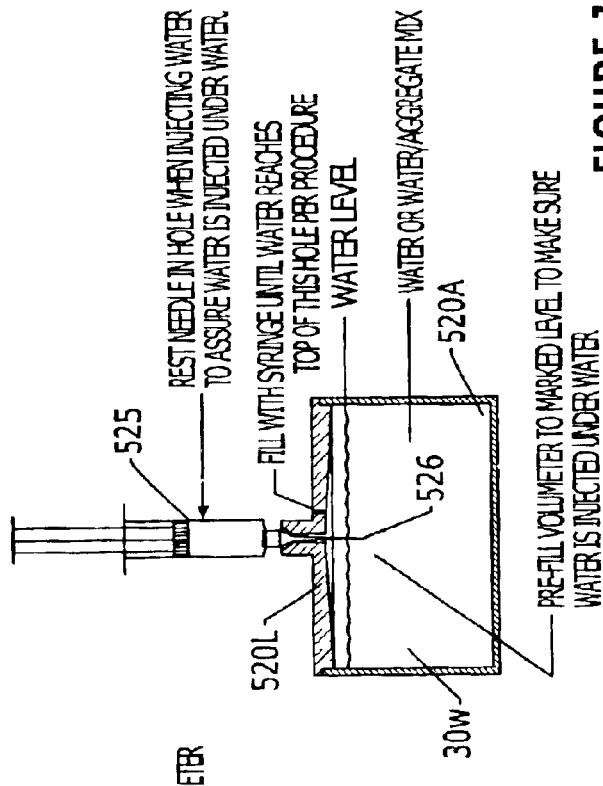
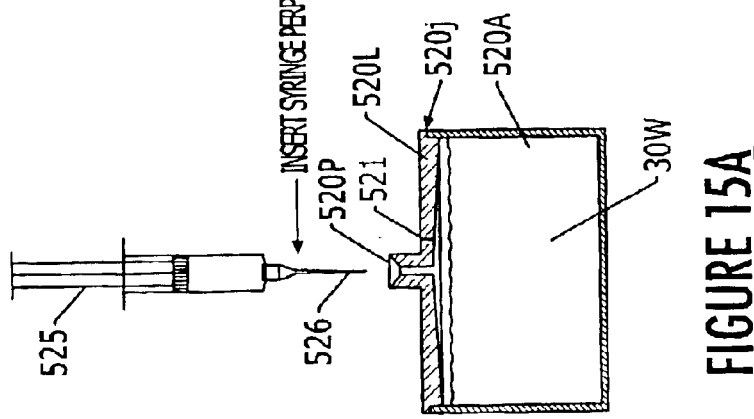

SYSTEMS AND METHODS FOR DETERMINING THE ABSORPTION AND SPECIFIC GRAVITY PROPERTIES OF COMPACTED AND LOOSE MATERIAL INCLUDING FINE AND COARSE AGGREGATES

RELATED APPLICATIONS

This application is a divisional of U.S. application Ser. No. 09/976,530, filed Oct. 11, 2001, now U.S. Pat. No. 6,515,643 which claims the benefit of priority from U.S. Provisional Patent Application Ser. No. 60/240,563 filed Oct. 13, 2000, the contents of which are hereby incorporated by reference as if recited in full herein.

FIELD OF THE INVENTION

This invention is related to methods and systems used to determine the specific gravity, absorption, and/or porosity characteristics of compacted and loose materials including aggregate materials used in the construction of roads and structures as well as those obtained in connection with oil and geological explorations.

BACKGROUND OF THE INVENTION

Water absorption and specific gravity of aggregates are both parameters which are routinely analyzed in the design and construction of roads and structures worldwide. These parameters can also be important considerations in oil and geological explorations.

The ability to accurately measure water absorption and specific gravity of materials in a repeatable manner and in a relatively short time frame can be important for engineers and practitioners interested in assessing the suitability of bulk materials and material mixtures in their projects. For example, water absorption and specific gravity values can yield important information about the hydraulic properties of soils and aggregates.

In the asphalt mix design industry, the bulk specific gravity and absorption of aggregates in a particular design, which can include both fine and coarse aggregates, are important assessments of the quality and suitability of the asphalt design to a particular application. The design selection of materials can be a mixture or composition of various sized aggregates in an assortment of different materials which can be varied to yield the desired functional characteristics or standards. Bulk specific gravity can be used as a measure to assess the amount of asphalt binder absorbed by the aggregates and the percentage of voids in the mineral aggregates in the design; each of these parameters can be important considerations in assessing the quality of the materials or the suitability of the composition of the design.

Conventionally, test methods described in standards AASHTO T84 and ASTM C128 have been used to assess fine aggregates. Unfortunately, these methods can have poor repeatability. Generally stated, the conventional method requires that a material sample of fine aggregate (about 1000 g) is oven dried to a constant weight. The material sample is then immersed in water for a 24-hour saturation period. The sample is then spread on a flat surface and exposed to a gently moving stream of warm air until a saturated surface-dry condition is reached. To assess when the saturated surface-dry condition has been reached, the material sample is positioned into an inverted cone and lightly compacted. The cone is removed and if the material "slumps" the material sample is considered to be in a saturated surface-dry condition. The amount of "slump" that represents when the saturated surface-dry condition has been reached can vary from test-to-test and is operator-dependent. Some laboratories or agencies define this condition as one in which the slump corresponds to the diameter of a dime from the top of the cone. The amount of slump can be adjusted by repetitive drying of the aggregates until the desired slump is achieved. However, if the aggregate sample is over-dried during the test procedure, the sample must be re-saturated and the drying process repeated.

After the material sample has reached the saturated dry-surface condition, a portion of the material sample is placed in a flask, which is then filled with water to a calibrated level and weighed. The fine aggregate material sample is removed from the flask and oven-dried to a constant weight. The specific gravity (apparent and bulk) and absorption are then calculated based on the three measured weights (the weight of the oven-dried sample, the weight of the flask filled with water, and the weight of the flask with the material and specimen and water to a calibration mark).

Angular fine aggregates with high absorption characteristics and/or rough surface textures do not typically slump readily. Therefore, determining the saturated surface dry (SSD) weight for samples that include these types of materials can be difficult with the cone method described above. Unfortunately, incorrect determination of this parameter in the testing process can have undesirable effects on the performance or service life of the asphalt pavement or other structure made using incorrectly analyzed materials.

In the concrete industry, the same cone test is typically used to determine the SSD condition in fine materials to determine the proper amount of water to add to the concrete mixture. Proportioning the concrete mixture with an incorrect amount of water can negatively affect the strength and durability of the concrete structures.

The testing standards for coarse aggregates are described in AASHTO T85 and ASTM C-127. "Coarse" is typically associated with aggregates retained on a 2.36 mm (No. 8) or larger sieve. In order to obtain the SSD weight of these types of samples, these standards provide that the operator pads the aggregates with a towel and uses the towel-dried weight as the SSD weight of the sample. Again, this technique is subjected to operator variability, as if the material sample is not properly prepared—such as if improper washing or wetting of the sample, aggressive drying, or removing fine dirt particles off the surfaces of the aggregates (thus, potentially leaving the large aggregate surface wet)—the results of the analysis can vary and may not provide a reliable indication of the properties of the sample. Further, the towel-dry technique itself is a subjective procedure and the degree of dryness can vary from operator-to-operator and sample-to-sample.

Recently, a study was undertaken by the National Center for Asphalt Technology (NCAT) and was presented at the $79^{th}$ meeting of the Transportation Research Board, in January, 2000. In this study, the authors proposed a device to attempt to automate the determination of the SSD condition for fine aggregates as a replacement to AASHTO T84 and ASTM C128. The device included a spinning drum equipped with a hair dryer for drying the aggregates, a humidity indicator and a temperature sensor mounted inside the drum. In operation, a saturated material sample is placed inside the drum and the sample is spun while continuously monitoring temperature and humidity. The theory behind this technique is that a break in the response between temperature and time or humidity and time will indicate a saturation point. For example, continuous drying will occur until either the temperature or humidity stabilizes. At this "stability point", the aggregates are expected to be at the SSD condition. After the indicated response has stabilized, the temperature or humidity can continue to change, also indicating that the internal water has been removed (another indication that the SSD condition was achieved at the stability point). Unfortunately, in operation, the material can clump together inside the drum. When aggregates clump (fine aggregates can be particularly susceptible to clumping), the SSD condition may be unachievable. Indeed, fine aggregates can impede accurate determination of a true SSD condition as they have a tendency to stack up or attach to each other and not allow the surface of each individual aggregate to reach the desired SSD condition. Further, the stability point (defined as a plateau) in time versus temperature or humidity is an empirical derivation that may be difficult to ascertain or achieve with every aggregate type.

Recently, another device has been proposed by the Barnstead/Thermolyne Company of Boise, Id. to determine the SSD condition of fine aggregates. This device proposes placing approximately 500 g of dry aggregates in a vibrating dish. Water is introduced into the aggregate and an infrared device monitors the surface moisture. Again, the time response versus the infrared moisture reading is plotted and a point along the response line is identified and selected as corresponding to the SSD condition of the aggregates. Unfortunately, this method is also empirically based and can depend on the type and perhaps the gradation of aggregates. Also, the fine aggregate SSD may be difficult to reliably define for every aggregate type.

SUMMARY OF THE INVENTION

Embodiments of the present invention provide systems, methods, and devices that employ vacuum-sealed material samples and liquid displacement. The material sample can be divided into two portions and weights associated with each portion can then be obtained under various conditions and used to calculate the percentage absorption, the porosity, and/or the specific gravity (for fine and coarse aggregates, the term "density" is sometimes used instead of "specific gravity"). Alternatively, the same material sample portion can be serially analyzed and those results compared.

In certain embodiments, a calibration adjustment factor can be applied to the calculated percent absorption value determined as summarized above. The calibration adjustment factor can correspond to a particular aggregate type or mix being analyzed. The calibration adjustment factor can offset the amount of water that may be absorbed while the sample aggregate is wetted under water and the weight measured under water (typically, the higher absorptive materials will have higher correction factors compared to the lower absorptive materials). The calibration adjustment factor can be obtained by examining the amount of absorption as a function of time that the aggregate is exposed to a vacuum, or obtained by comparing the absorption due to an independent method.

Certain embodiments of the present invention are directed to methods of determining a material property such as the absorption or specific gravity of an aggregate material. The method comprises the steps of: (a) drying a first aggregate material sample; (b) determining the dry weight of the first aggregate material sample; (c) placing the first aggregate material sample in liquid in a first container; (d) adding liquid to the container with the first aggregate sample to fill the container to a desired volume; (d) measuring the weight of the first container holding the first aggregate material sample and the liquid after the step of adding liquid; (e) drying a second aggregate material sample; (f) determining the dry weight of the second aggregate material sample; (g) vacuum sealing the second aggregate sample in a second container; (h) immersing the second aggregate material sample while it is held in the sealed second container in the liquid bath; (i) opening the sealed second container as it is held immersed in the liquid bath; (j) measuring the weight of the second aggregate material sample and the second container while they are held immersed in the liquid bath; and (k) determining at least one material property of the aggregate undergoing analysis based on the weights obtained in the two measuring steps.

In certain embodiments, the first and second samples are different samples of substantially the same weight selected such that they are both representative of the aggregate material undergoing analysis. In other embodiments, the first and second samples are the same sample of the aggregate material undergoing analysis.

Other embodiments are directed to methods for analyzing material properties of a material sample comprising aggregate. The method includes: (a) providing a first and second aggregate material sample of a material undergoing analysis; (b) drying the first aggregate material sample; (c) determining the dry weight of the first aggregate material sample; (d) providing a volumetric container, the volumetric container having a lid that attaches thereto to define a fixed internal volume of the volumetric container; (e) partially filling the volumetric container with liquid; (f) placing the first aggregate material sample in the volumetric container; (g) adding additional liquid to the container after the first aggregate material is placed in the volumetric container; (h) attaching the lid onto the volumetric container to enclose the liquid and aggregate material therein; (i) measuring the weight of the volumetric container holding the first aggregate material sample and the liquid after the steps of attaching the lid and adding additional liquid; (j) encasing the second aggregate sample in a vacuum-sealed container; (k) immersing the second aggregate material sample while it is held in the sealed container in a liquid bath; (l) opening the sealed container as it is held immersed in the liquid bath; (m) measuring the weight of the second aggregate material sample and the container while they are held immersed in the liquid bath; and (n) determining at least one of the percent absorption, apparent specific gravity, bulk specific gravity, and saturated surface dry (SSD) weight of the aggregate undergoing analysis based on the weights obtained in the measuring steps.

In particular embodiments, the lid of the volumetric container comprises a liquid entry port, and the step of adding additional liquid comprises: (a) adding a first amount of additional liquid to a level that is below the top of the volumetric container; and (b) after the step of attaching the lid, adding a second amount of liquid into the volumetric container through the liquid entry port so that the liquid with the aggregate fills the container and occupies the fixed internal volume.

Still other embodiments of the present invention are directed to methods of obtaining absorption or porosity data for an aggregate sample. The method includes: (a) providing a material specimen for analysis comprising aggregate; (b) dividing the material specimen into at least two samples, a first aggregate sample and a second aggregate sample; (c) wetting the first aggregate sample; (d) obtaining a weight of the wetted first aggregate sample; (e) encasing the second aggregate sample in a vacuum-sealed collapsible bag; (f)

immersing the encased vacuum sealed second sample in liquid; (g) opening the bag while immersed to allow liquid to enter the bag; (h) obtaining a weight of the opened bag with the second sample while immersed in the liquid; and (i) evaluating the weight of the wetted first sample and the weight of the second sample in the opened bag in the liquid.

Certain embodiments of the present invention include methods of determining the absorption or porosity of an aggregate material. The method includes the steps of: obtaining a first aggregate material sample of an aggregate material undergoing analysis; obtaining a second aggregate material sample of the aggregate material undergoing analysis; drying the first and second aggregate material samples; determining the dry weight of at least one of the first and second aggregate material samples; immersing the first aggregate material sample in a liquid bath so that the first aggregate material sample is wetted; measuring the weight of the first aggregate material sample while immersed in the liquid bath; vacuum sealing the second aggregate sample in a container; immersing the second aggregate material sample while it is held in the sealed container in the liquid bath; opening the sealed container as it is held immersed in the liquid bath; measuring the weight of the second aggregate material sample and the container while they are held immersed in the liquid bath; and determining the absorption of the aggregate undergoing analysis based on the weights obtained in the first and second measuring steps.

The second material sample can be held in a collapsible vacuum-sealed bag while the first material sample can be placed in a rigid container or directly into the liquid bath container.

The method can be used for construction materials (loose or compacted) including fine and coarse aggregate materials or material mixtures as well as for porous and highly porous materials.

Other embodiments of the present invention include computer program products for determining the absorption and/or specific gravity value of an aggregate sample undergoing analysis. The computer program product includes a computer readable storage medium having computer readable program code embodied therein and comprises (a) computer readable program code for accepting input corresponding to first and second measurements of first and second aggregate sample weights corresponding to an aggregate sample undergoing analysis; and (b) computer readable program code for calculating the absorption value based on the first and second measurements.

Still other embodiments are directed to computer program products for determining absorption characteristics and/or specific gravity value of an aggregate sample undergoing analysis. The computer program product comprises computer readable storage medium having computer readable program code embodied in said medium, said computer-readable program code comprising: (a) computer readable program code for accepting input corresponding to weight measurements of first and second aggregate samples obtained under dry and different wet conditions corresponding to an aggregate sample undergoing analysis; (b) computer program code defining predetermined mathematical relationships for determining the material parameters of interest; and (c) computer readable program code for calculating at least one of the percent absorption value, the apparent specific gravity, the bulk specific gravity, the saturated surface dry weight, and the porosity, based on the dry and wet measurements of the first and second samples and the pre-determined relationships.

Additional aspects of the present invention are directed to apparatus for evaluating aggregate samples. In certain embodiments the apparatus includes a rigid volumetric container having at least one upwardly extending wall and a closed bottom and open top portion. The container may include a lid configured to securely attach to the volumetric container top portion, so that, when attached, the volumetric container and lid define an enclosed internal fixed volume. The apparatus includes a quantity of liquid and aggregate material positioned in the volumetric container. In operation, the liquid and aggregate are presented in sufficient quantity so as to occupy substantially the entire internal fixed volume and exhibit a corresponding weight.

The volumetric container or apparatus can be formed as a pycnometer device having a glass or translucent/transparent body with a reduced-size neck portion that defines an internal constant or fixed volume. The neck portion can be formed into a lid that attaches to an underlying body. The neck can be configured in the lid so that it is substantially vertically oriented and has a visible fill line marking. The neck can terminate into an open port that allows liquid to be inserted therethrough.

The apparatus can include a holding fixture. The fixture includes a planar base configured to receive the volumetric container thereon and a plurality of upwardly extending clamp platforms affixed to the base and disposed in spaced apart alignment thereon. The clamp platforms are arranged to be proximate or to abut the outside wall of the volumetric container when the volumetric container is placed on the base of the fixture. The fixture also includes at least one clamping mechanism disposed on each clamp platform. The platforms have a height sufficient to position the clamping mechanism over the top surface of the lid, such that, when in position, the clamps force the lid down onto the volumetric container.

Other embodiments of the invention are directed to systems for analyzing aggregate samples. The system includes: (a) a volumetric container with a detachable lid, the lid having a syringe access port formed therethrough; (b) a syringe having a body adapted to hold liquid therein and a lumen length sufficient to extend below the lid (and under the surface of the liquid) when in position in the access port; and (c) computer program code for determining percent absorption and specific gravity of fine or very fine aggregate samples.

Other embodiments include systems for analyzing aggregate samples that include a volumetric container with a detachable lid that together define a fixed internal volume and computer program code for determining percent absorption and/or specific gravity of aggregate samples based on a first weight obtained of the volumetric container with the lid attached and full of liquid and a second weight obtained of the volumetric container with the lid attached and full of liquid and an aggregate material sample.

Still other embodiments are directed to systems with the computer program code being selectable by the user depending on whether coarse or fine aggregates are being analyzed.

Additional embodiments are for systems for analyzing aggregate samples that include: (a) a rigid container with a detachable lid defining an internal volume; (b) at least one flow path located in an upper portion of the container; (c) a vacuum source in fluid communication with the container; and (d) computer program code for determining percent absorption and/or specific gravity of aggregate samples based on a first weight obtained of the container with the lid attached with liquid and an aggregate material sample located at a bottom portion thereof with the liquid level extending above the aggregate.

The system may include at least one valve positioned in the flow path between the container and the vacuum source.

Yet another embodiment is a system for analyzing aggregate samples comprising: (a) a container with a detachable lid defining an internal volume; (b) a pressure source in fluid communication with the container; (c) at least one flow path located in an upper portion of the container in communication with the pressure source and the container; and (d) computer program code for determining percent absorption and/or specific gravity of aggregate samples based on a first weight obtained of the volumetric container with the lid attached with liquid and an aggregate material sample located at a bottom portion thereof with the liquid level extending above the aggregate.

In particular embodiments, the pressure source is a piston. In certain embodiments, the system can include a subcontainer configured to hold the aggregate inside the container, and a scale held inside the container above the liquid level, the scale being configured with an arm that suspends the subcontainer above the bottom of the container.

The computer program product may also include one or more of computer readable program code for assigning an absorption correction factor to the calculated absorption value based on the absorption characteristics of the aggregate material undergoing analysis and code for determining the specific gravity of the aggregate material undergoing analysis based on the first and second density data input.

The techniques provided by the present invention can avoid direct determination of the mass of the sample at the SSD condition, which, as noted above, can be difficult to define with fine aggregates. Advantageously, the test methods and systems of the present invention are repeatable and can reduce or inhibit operator variability. Further, the systems and methods of the present invention can reduce the amount of active testing time, typically down to a time on the order of 10–30 minutes. A 24-hour saturation period is not required and the methods and systems can be used with both fine and coarse aggregates as well as with both high and low porosity aggregates and other material such as ceramics and other formed graded materials.

Other embodiments of the present invention include systems and methods for determining the material property characteristics of a material sample such as, apparent specific gravity or density of a material. The method includes obtaining a material sample of an construction material undergoing analysis; drying the material sample; determining the dry weight of the material sample; determining the calibrated volume of a container; placing the material sample into the container; evacuating the container with the sample held therein; introducing liquid into the container so that the material sample is held immersed under the liquid in the container after the evacuating step; measuring the weight of the material sample and the container while the sample is held immersed in the liquid in the container; and determining the apparent density of the sample based on the dry weight of the sample, the calibrated volume of the container, and the weight obtained during said measuring step.

Still other embodiments include systems and methods for determining material property characteristics of a material such as the apparent specific gravity, porosity, or absorption characteristics of a material. The embodiments can include, similar to the embodiment described above, obtaining a material sample of a construction material undergoing analysis; drying the material sample; and determining the dry weight of the material sample. The method can also include the steps of placing the material sample into subcontainer; positioning the subcontainer and the material sample in a container; introducing liquid into the container so that the material sample and the subcontainer are held immersed under the liquid in the container; measuring a first weight of the material sample and the container while the sample is held immersed in the liquid in the container at atmospheric pressure; evacuating the container with the sample held in the subcontainer positioned therein; measuring a second weight of the material sample and the container while the sample is held immersed in the liquid in the container after said evacuating step; and determining a first density and second density and/or absorption of the material sample based on the weights obtained during said measuring steps.

In another embodiment, the evacuating step can be replaced with a pressurizing step whereby the pressure in the container is elevated with the sample held in the subcontainer positioned therein and the second weight of the material sample and the container is measured while the sample is held immersed in the liquid in the container with the pressure elevated above atmospheric pressure.

Certain embodiments of the methods of the present invention may be able to assess other physical parameters associated with the material sample, such as, but not limited to, the permeability of material samples, the porosity of material samples, the apparent specific gravity, the maximum density, the maximum specific density and other related measurements or parameters. Further, the analysis may be automated so that the scales, vacuum equipment, or other machinery can be integrated to directly input desired measurement data to a computer processor that can then calculate the desired parameter and output the information to the operator.

The above summary is not intended to limit the scope of the invention as other apparatus and fixtures can also be used to carry out the methods of the present invention.

The foregoing and other objects and aspects of the present invention are explained in detail in the specification set forth below.

BRIEF DESCRIPTION OF THE DRAWINGS

FIG. 10A is a data collection table illustrating data obtained for determining specific gravity, porosity, and/or absorption according to embodiments of the present invention.

FIG. 10B is a data collection table illustrating data obtained for determining specific gravity, porosity, and/or absorption according to embodiments of the present invention.

FIG. 15A is a front sectional view of a volume container according to embodiments of the present invention.

FIG. 15B is a front sectional view of the device shown in FIG. 15A illustrating a syringe in position according to embodiments of the present invention.

DESCRIPTION OF EMBODIMENTS OF THE INVENTION

Figure 1:
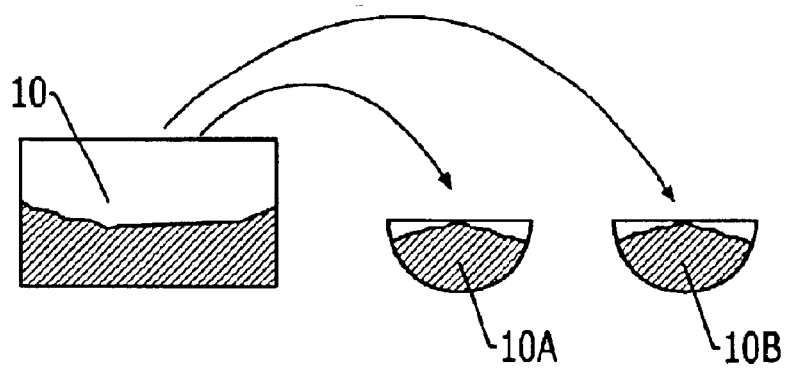
FIG. 1 is a front top perspective view of an aggregate sample divided into first and second portions.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers may be exaggerated for clarity. In the block diagrams, broken lines indicate such operation or feature is optional.

Generally stated, embodiments of the present invention employ two measurements of aggregate weights based on a (initially) dry sample(s). The weight measurements can be obtained by splitting the sample into two or more samples. Alternatively, a single (the same) sample can be analyzed serially to obtain the weights and values used to determine the desired parameter(s). For ease of discussion, the present invention will be described as using two different samples for clarity of description.

The weights of the two samples are obtained under different conditions (or the one sample is weighed at different times under different conditions) and these values can be used to determine the desired material parameter. One of the samples is used to determine a first weight or density value (corresponding to an apparent density) and the other is used to determine a second weight or density value. The two density values are then used to determine the desired material parameter or property. For example, the two weights can be used to calculate the percent absorption without directly measuring the mass at SSD (which can be difficult to determine, particularly for fine aggregates).

The specific gravity of an aggregate can be stated to be the ratio of the weight of a unit volume of material to the weight of the same volume of water at about 25° C. (typically from about 20°–25° C.). Other liquids and temperatures can be used in the analysis with the appropriate correction factors/adjustments made to the ratio. There are three generally accepted types of specific gravity for the aggregate: apparent specific gravity, bulk specific gravity, and effective specific gravity. Apparent specific gravity considers the volume as being the volume of the aggregate sample itself and does not include the volume of any pores, voids, or capillaries that become filled with water when saturated (such as during a 24 hour soak period). Bulk specific gravity considers the overall volume of the aggregate sample including the pores, voids, and capillaries that become filled with water when soaked. The effective specific gravity considers the overall volume of the aggregate exclusive of the volume of pores that absorbs asphalt and can be approximated as the weighted average of the apparent and bulk specific gravity.

For asphalt applications, air voids in the compacted asphalt pavement appear in the mix as small pockets of air between the asphalt coated aggregate particles. Thus, when designing a particular mixture for an application, the choice or selection of the specific gravity may have a substantial impact on the calculated amount of air voids in the mixture. The actual or real specific gravity of the aggregate in the mixture will depend on the absorptivity of the aggregate (the amount of asphalt the aggregate in the mixture will absorb).

Absorption relates to the porosity of an aggregate and is generally represented by the amount of water (or other specified liquid) it absorbs when soaked in water (or other liquid). A porous or absorptive aggregate can absorb asphalt, which may make an asphalt mixture dry or less cohesive. To compensate, an additional amount of asphalt can be added to the paving mixture when a porous aggregate is used in the design. It is also noted that very porous aggregates may require a significant amount of additional asphalt because they tend to have high absorption rates. In certain applications, highly absorptive or porous aggregates are used when they possess other desirable qualities. For example, blast furnace slag and other synthetic and manufactured aggregates are lightweight and highly porous. Their lightness and wear-resistant properties still make them desirable for use in many pavement construction projects.

Turning now to the figures, FIG. 1 illustrates a material sample 10. The material sample, which can be an aggregate material sample, 10 can be selected such that it is representative of the material mixture and may be obtained according to the procedures described in C 702 (as referenced in ASTM C128). The aggregate material sample 10 may include both fine and coarse aggregates (and may also include dust or mineral filler), which can be separated and graduated according to well-known procedures, as needed for the material sample undergoing analysis. The aggregate material sample may also contain a plurality of different aggregate composition types.

Embodiments of the present invention can be used for both fine and coarse aggregate assessments. As noted above, the term "coarse aggregate" is typically applied to mineral and/or synthetic aggregate material that is retained on a 2.36 mm (No. 8) sieve. The term "fine aggregate" applies to material passing through the 2.36 mm (No. 8) sieve. Mineral filler or fine aggregate (including "very fine" aggregate) is applied to material of which at least 70% passes through a 75 $\mu$m (No. 200) sieve. Asphalt pavement and/or asphalt concrete specifications typically require that the aggregate particles are within a certain range of sizes and that each size is present in a certain proportion. The aggregate mixture may include aggregates of different shapes as well as aggregates of different material types. For example, many asphalt mixtures contain both angular and rounded aggregate particles. The coarse aggregate particles can be a crushed stone or gravel and the fine aggregate can be a natural sand (round particles) or stone screenings. The term "porous or absorptive materials" includes materials that have a tendency to have voids, such as asphalt coated aggregate particles, and/or materials which have greater than or equal to about 2% by weight absorption.

The sample 10 can be selected such that it is sized on the order of between about 100–5000 g which is then divided into at least two substantially equal portions. For example, two portions between about 50–2500 grams, and more typically between about 1000–2000 grams each. Alternatively, one of the sample portions 10A, 10B may be selected such that it is smaller or larger than the other. Further, for composition mixtures comprising larger sized coarse aggregates, each sample portion size may approach 4000 grams or more.

The calculations, which will be discussed below, for each of the weight-based measurements (densities), can be independently determined without regard to the particular weights used for each sample.

In certain embodiments, a material sample of at least about 2000 grams is obtained. As shown, the sample 10 can be subdivided into two representative samples 10A, 10B. The sample 10 or the two subdivided samples 10A, 10B are completely dried according to well-known procedures. In certain embodiments, each of the first and second samples 10A, 10B are subdivided from the parent sample 10 in substantially equal amounts. For ease of discussion, these samples 10A, 10B will be described as being 1000 g each. Other quantities of the sample 10 and sample portions 10A, 10B can be used as long as they are substantially representative of the material being analyzed.

Figure 2:
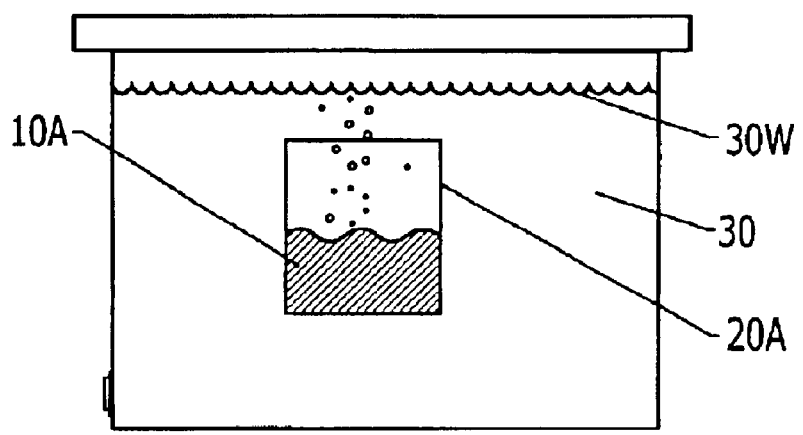
FIG. 2 is a side perspective view of the first divided portion of FIG. 1 positioned in a container with liquid introduced according to embodiments of the present invention.
Figure 17:
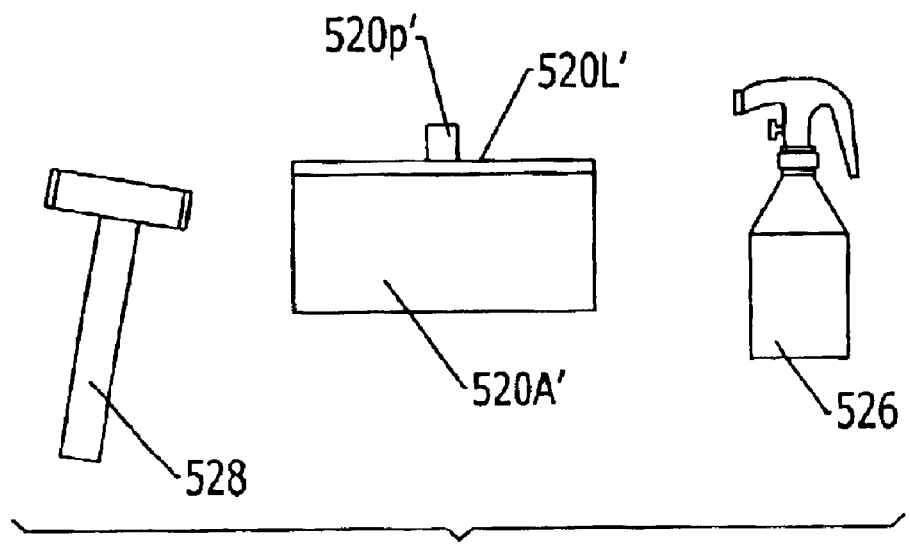
FIG. 17 is a front perspective view of an aggregate volume container and implements according to additional embodiments of the present invention.
Figure 19:
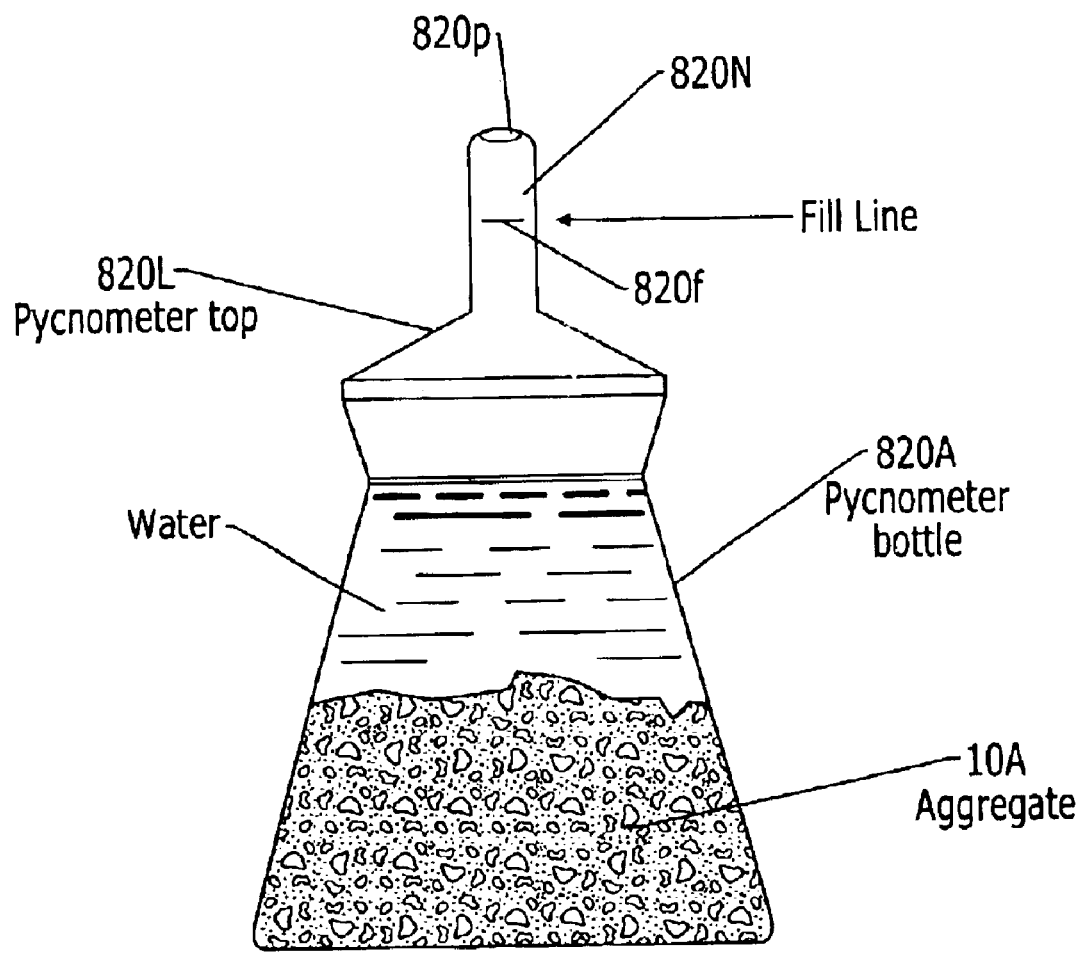
FIG. 19 is a front view of a pycnometer or aggregate volume container according to still additional embodiments of the present invention.

The dry weight of the first sample 10A is obtained. The first sample 10A is then inserted or placed into a container 20A as shown in FIG. 2. The weight and volume of the container 20A is determined (preferably in a dry condition and before the first sample is positioned therein). The weight of the sample 10A in the container 20A can also be obtained (or this weight can be obtained as an alternative to obtaining the weight of the dry sample alone). The container 20A can be a flexible or collapsible bag or a rigid or semi-rigid container. In certain embodiments, such as shown in FIGS. 14B, 17, 19 the container 520A, 520A', 820A can be a liquid bath (primary) container itself such that the material specimen is placed directly therein and covered with liquid. In other embodiments, the container is actually a sub-container that can be placed in a primary container such as the liquid bath container.

In the embodiment shown in FIG. 2, after the sample 10A is placed in the container 20A, the container 20A and the aggregate sample 10A are slowly lowered into the liquid bath 30 until they are submerged. An operator can agitate the aggregate sample 10A in the container 20A such as by gently feathering the water over the sample or moving the sample around in the container, by hand, to cause the liquid or water 30w in the liquid bath 30 to fill the air spaces between the aggregate. Care should be taken during this operation to remove all large air bubbles from the bag as the bag is immersed into the liquid bath 30.

Figure 3:
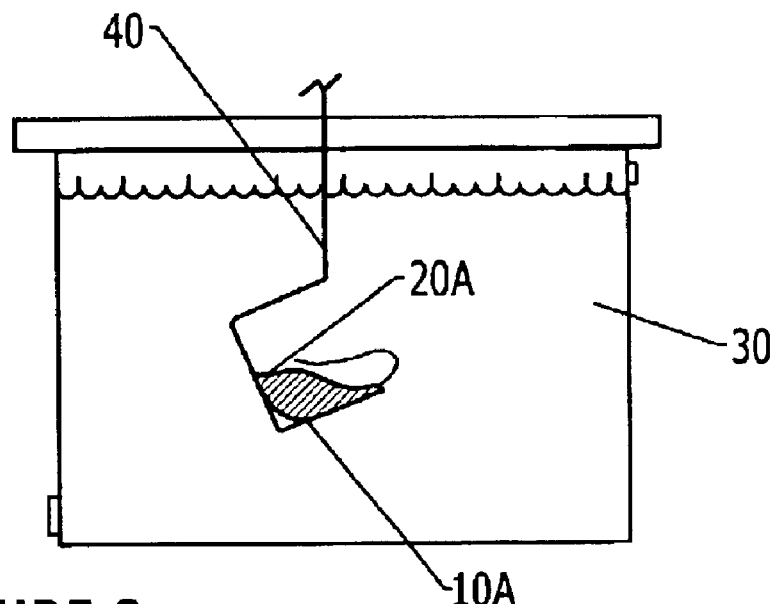
FIG. 3 is a top view of the container and first sample portion shown in FIG. 2 weighed according to embodiments of the present invention.

As shown in FIG. 3, a lift 40 is used to lower the sample 10A and the container 20A into the liquid bath 30. Once submerged and after the scales have stabilized, the weight of the container 20A and sample 10A under water is obtained. The scales (not shown) can be operably associated with the lift (to weigh based on the suspended weight) or with the bottom of the liquid bath to weigh the change in the liquid bath before and after the container 20A and specimen are submerged therein.

In other embodiments, as shown for example in FIG. 15A, the sample 10A can be placed into a volume container 520A (the sample is not shown in the container in this figure for clarity of discussion). The volume container 520A is configured with a lid 520L that can be securely attached to the body of the container 520A after the material sample 10A and a certain quantity of liquid have been introduced therein. In the embodiment shown in FIG. 15A, the lid 520L of the volume container 520A includes two fluid ports, a primary (inlet) port 520p and a secondary port 521. The secondary port 521 can be formed of a limited channel size, such as about ⅛–⅙ inches or less. This device 520A may be particularly suitable for evaluating material samples comprising fine aggregates. As will be discussed further below, the container 520A can be partially filled with liquid and the sample 10A then added thereto in a manner such that air between particles can be removed. Additional liquid can then be added so that the liquid 30w and sample 10A occupy the same volume as the volume of the container determined by liquid alone (i.e., the filler materials fill the internal volume of the container 520A defined by the internal volume after the lid has been placed thereon).

In particular embodiments, such as for evaluating material specimens comprising fine aggregates, air can be removed from between the particles by gently stirring the sample 10A in the container 520A while taking care to keep the sample 10A under the liquid surface. Then, liquid can be added to a predetermined volume (that may be noted by a mark or other indicia on the container 520A itself). The sample 10A should be completely submerged before stirring. The lid 520L can be placed on the container 520A to enclose the liquid and material sample 10A therein. Then, to completely fill the volume, liquid can be added via fluid port 520p until liquid can be seen in the top portion of (or bleeds from) port 521. The liquid should be introduced under the liquid surface level. In particular embodiments, as shown in FIG. 15B, a syringe 525 can be inserted into the port 520p such that its lumen 526 is sufficiently long to discharge the fluid under the liquid surface level.

After filling, any moisture or excess liquid that is proximate the port 521 can be dried or removed. In particular embodiments, where liquid has exited the joint 520j (FIG. 15A) between the lid and container body, care should be taken so as not to disrupt or remove this moisture or liquid. The container 520A with the sample 10A and filled volume (liquid) can be weighted to obtain a total weight. FIG. 10B illustrates a sample data worksheet that can be used by the operator or digitally performed to determine the desired material property parameters.

The container 520A and lid 520L can be configured in any suitable volume size and can be formed of any suitable rigid material, including, but not limited to, metal and/or glass. The lid 520L should be secured to the body of the underlying container 520A and should be configured so that it is sufficiently rigid so that it does not yield or deform when the inner volume of the enclosed container is filled with liquid or liquid and aggregate samples.

Figure 14A:
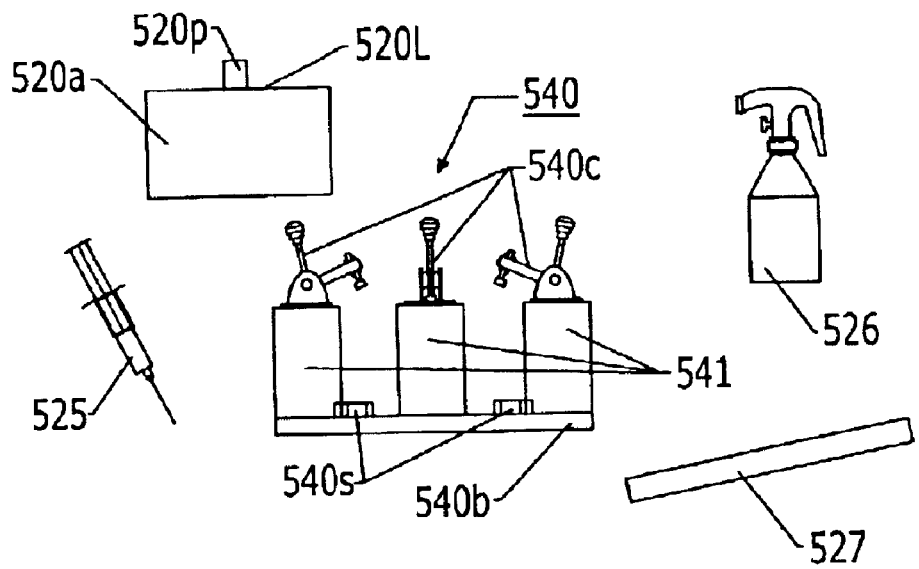
FIG. 14A is a front view of an apparatus comprising an aggregate volume container, a securing fixture, and other implements for evaluating material specimens according to embodiments of the present invention.
Figure 14B:
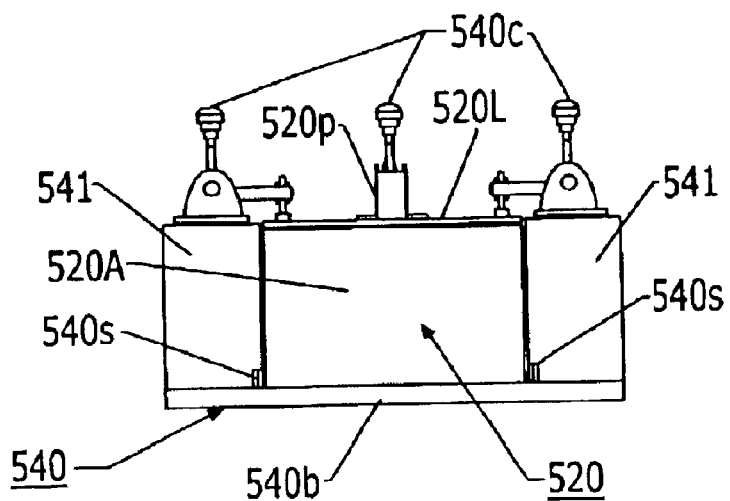
FIG. 14B is a front view of the volume container and securing fixture shown in FIG. 14A with those components assembled according to embodiments of the present invention.

FIGS. 14A and 14B illustrate that a container holding fixture 540 can be used to secure the lid 520L to the container 520A so as to inhibit the entry of air at the seal. As shown, the fixture 540 includes a platform surface or base 540b and a plurality of upwardly extending clamps 540c. The base 540b is planar and configured to hold the container 520A thereon. The clamps 540c rest on upwardly extending platforms 541 that position the clamps 540c vertically above the base a distance generally corresponding to the height of the lid 520L. The clamp platforms 541 are arranged on the base 540b so as to be positioned proximate the outer wall of the container 520A when the container is positioned thereon. As shown, stops 540s may also be used to provide alignment indicia on the platform 540b. A stirring implement such as a metal spatula 527 may be used to help evenly distribute the aggregate sample about the bottom of the container 520A.

In position, the clamps 540c are configured to be able to contact the perimeter outer surface of the lid 520L and impart a compressive downward force onto the lid 520L so as to substantially seal the joint 520j and inhibit the liquid from exiting therefrom, even when the container volume is full (at capacity) of liquid and/or liquid and aggregate. The fixture 540 and the closed container 520A can be put on the scales and weighed together. The weight attributed to the fixture 540 and container 520A as well as the liquid can be adjusted for in the calculation/analysis.

The lid 520L should be attached to the body and configured in a manner so that it does not yield or deform when the inner volume is filled with liquid or liquid and aggregate samples. Of course, other sealing means and/or container configurations can also be used, for example, O-rings, gaskets, threaded mating members, and the like. In other embodiments, the base 540b can be otherwise configured, such as with a recessed portion to receive the container 520A therein. In addition, clamps, where used, can be attached to tables or the container and lid themselves without using platforms or bases. However, the use of the stationary fixture reduces the variables in the measurements by providing repeatable, consistent procedures to obtain the volumetric weights.

For coarse aggregate evaluations, a similar volumetric container 520A' can be used as shown in FIG. 17. In this embodiment, the container lid 520L' is not required to have the port or 521 but can have port 520p. In addition, neither does the fixture 540 need to be used to secure the lid onto the body of the container 520A'. However, as shown in FIG. 17, the container 520A' may include a post that may be configured to define a port 521p'. In operation, the container 520A' can be partially filled with liquid (typically filled about half way with water), then the coarse aggregate sample placed therein (such as about 2000 +/−1 gram). The coarse aggregates can be manipulated so as to be substantially evenly distributed about the container 520A'. In particular embodiments, a rubber mallet 528 can be used to hit the container at about equal intervals about the outside wall (such as about at 90 degree increments) to attempt to cause the aggregate to position more evenly therein and/or to dislodge trapped air from the sample. Other agitation, rotation, or distribution means can also be employed for either of the methods described above.

For each of the above embodiments, an anti-foam or anti-bubble formulation can be sprayed onto or introduced over the surface of the water or liquid to reduce or inhibit air bubbles at the surface before the lid 520L, 520L' is placed onto the container 520A, 520A'. As shown, a spray bottle 526 may be filled with a suitable spray, solution or formulation such as isopropyl alcohol.

In any event, additional liquid can be introduced into the container 520A' so as to fill any remaining space with liquid. The lid 520L' can be aligned and seated properly so as to attach to the container body and define an enclosed volume. Excess liquid or water can exit the port 520p'. The container outer surface (top and sides) can be dried (such as with air or a towel). The filled closed container 520A' can then be weighed.

FIG. 19 illustrates another embodiment of a volumetric container 820A. In this embodiment, the container 820A includes a lid or top 820L that includes visual or optical indicia of liquid level (fill line) 820f thereon. As such, the lid can be formed of a material that allows the liquid level to be visually or optically compared to the fill line 820f. This can allow the container 820A to be repeatedly filled to a constant fixed volume reliably. Other means of providing consistent fill levels can also be used (such as pressure or liquid sensors/floats and the like). In certain embodiments, the lid 820L is translucent or transparent such as formed of glass or other substantially rigid transparent or translucent material so as to be able to remain seated and hold its shape when liquid is filled to the fill line 820f. The container body 820A can also be formed of glass. The container 820A and lid 820L can be termed a particular type of volumetric container, namely, a "pyconometer". As shown, upper portion of the lid 820L can include a region that has a reduced cross-sectional width compared to the width or cross-sectional area of the underlying container 820A. As shown, the region is less than about 30% the cross-sectional width to define a relatively narrow neck 820N. The neck 820N can be oriented to be substantially vertical and so that the upper end portion includes an open-end portion 820p, through which liquid can be added to the fill line 820f after the lid is attached to the body, 820L, 820A, respectively, as needed. In operation, liquid and an aggregate sample 10A can be disposed into the container 820A in a sufficient quantity to occupy substantially the entire internal defined constant or fixed volume and to exhibit a corresponding weight. This type of volumetric container 820A can be used for both coarse and fine aggregate evaluations.

Figure 4:
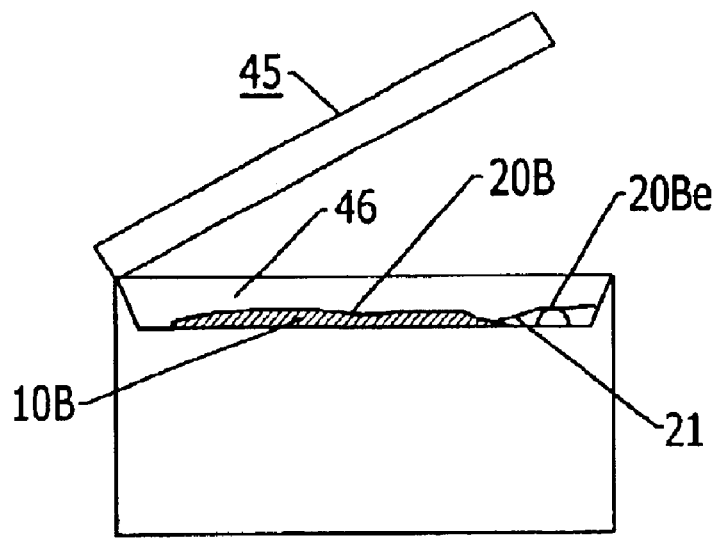
FIG. 4 is a top front perspective view of the second divided portion of FIG. 1 placed in a different bag and then positioned to be vacuum sealed in a vacuum chamber according to embodiments of the present invention.

In certain embodiments, another different or second container 20B, as shown in FIG. 4, is used to hold the second sample 10B. The dry weight of this sample 10B can be measured before it is placed in the second container 20B. Alternatively, the dry weight of the sample 10B held in the container 20B can be measured. As shown, the second container 20B can be a flexible bag that is able to conform to the contour of the sample held therein when exposed to an evacuating and sealing process. The bag may be an elastomeric, plastic bag, elastomeric/foil lined bag, or other water resistant material bag. Suitable bags identified as Corelok® bags are available from InstroTek, Inc., located in Raleigh, N.C. Other container types can be used as long as they are configured to allow water to enter in after reaching an evacuated state with the material sample held therein. For fine aggregates, care should be taken to retain the fine aggregates in the container during the weight measurements when water enters the container to wet the sample.

In certain embodiments, the sample 10B is positioned in the bag 20B such that it is consistently spread across the width or area of the container away from the open end or edge portion 21 which can be subsequently sealed along a sealing edge portion 20Be.

For example, particularly for coarse aggregate samples, a physical spreading of the sample may be needed before or after it is placed in the vacuum apparatus so as to make the aggregate layer substantially flat. Further an inner compressible "channel" bag may be used to help inhibit punctures during handling. The channels are small surface (rough) patterned channels configured in the bag to help direct air out thereof during the evacuation process. Typically, only the outer bag 20B is sealed (the inner bag fits within the outer bag such that its end does not overlie the sealing strip). See, e.g., U.S. patent application Ser. No. 09/580,792 the contents of which are hereby incorporated by reference as if recited in full herein.

The bag 20B and the sample 10B are placed in or connected to be in fluid communication with a vacuum apparatus. As shown in FIG. 4, the sample 10B in the bag 20B is placed in the chamber 46 of a vacuum apparatus 45 and oriented such that the open edge portion 21 is positioned so that at the proper time in the evacuation process, the open end of the bag 21 will be automatically sealed at the sealing edge portion 20Be while held in the vacuum chamber 45. A suitable vacuum apparatus identified as a CoreLok™ vacuum apparatus is available from InstroTek, Inc., located in Raleigh, N.C. Further descriptions of the vacuum apparatus and methods and bags are described in co-pending and co-assigned U.S. patent application Ser. No. 09/580,792 the contents of which were incorporated by reference above.

Figure 5:
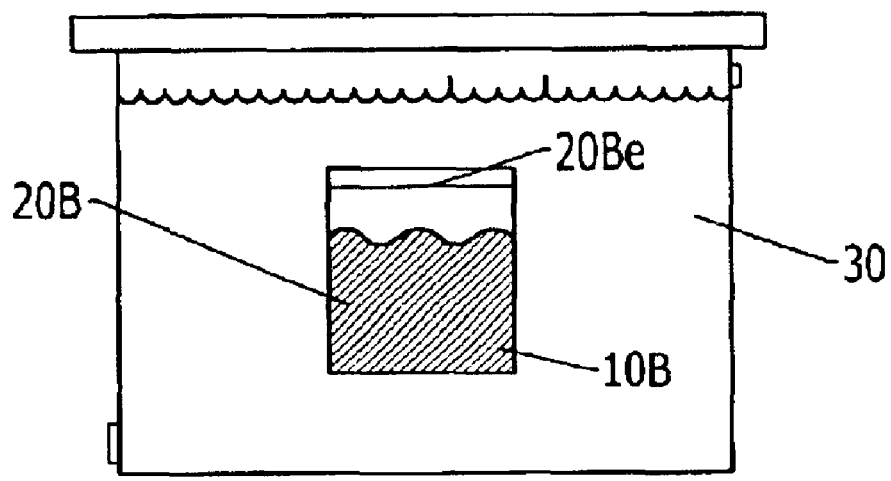
FIG. 5 is a front view of the evacuated sealed bag holding the second portion as the evacuated bag and sample are held submerged in the liquid bath according to embodiments of the present invention.
Figure 6:
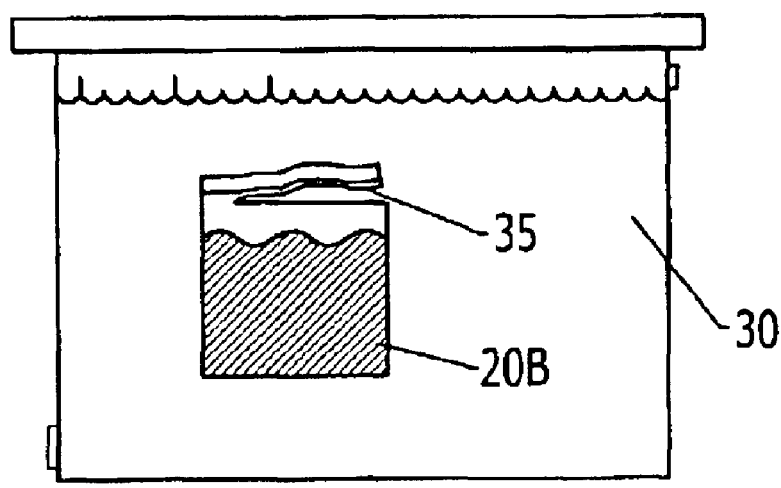
FIG. 6 is a front view of the bag and sample of FIG. 5 illustrating an opening being introduced to the evacuated sealed bag as the bag is held submerged under the liquid according to embodiments of the present invention.
Figure 7:
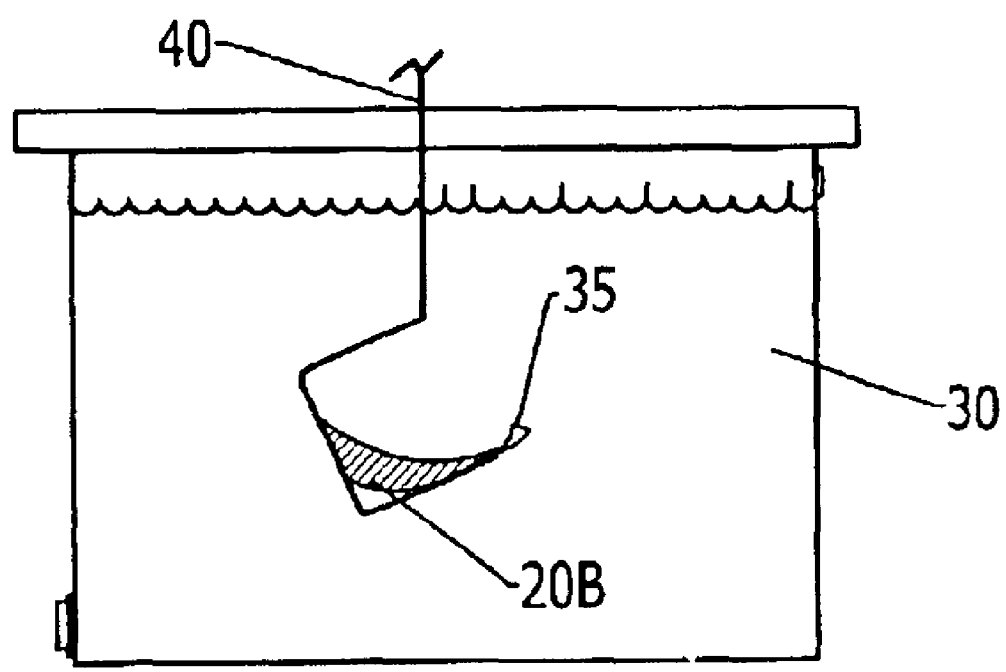
FIG. 7 is a top view of the opened bag held in the liquid bath while the weight is obtained.

After the evacuated sample is sealed in the bag 20B, it is removed from the vacuum chamber 46 and held under water such that it is submerged into the liquid bath as shown in FIG. 5. The sealed bag 20B is opened while the bag and sample 10B are held submerged under water. The bag 20B can be opened by cutting, tearing, puncturing, or otherwise compromising the sealed integrity of the bag. Thus, at least one opening 35 is inserted into the bag 20B. The opening 35 can be positioned about ¼–½ inch under the seal 20Be. After inserting the opening into the bag 20B, the bag walls can be separated or pulled gently apart to allow water to enter therein, with care being taken to hold the sample 10B and the bag 20B completely under water.

Figure 16A:
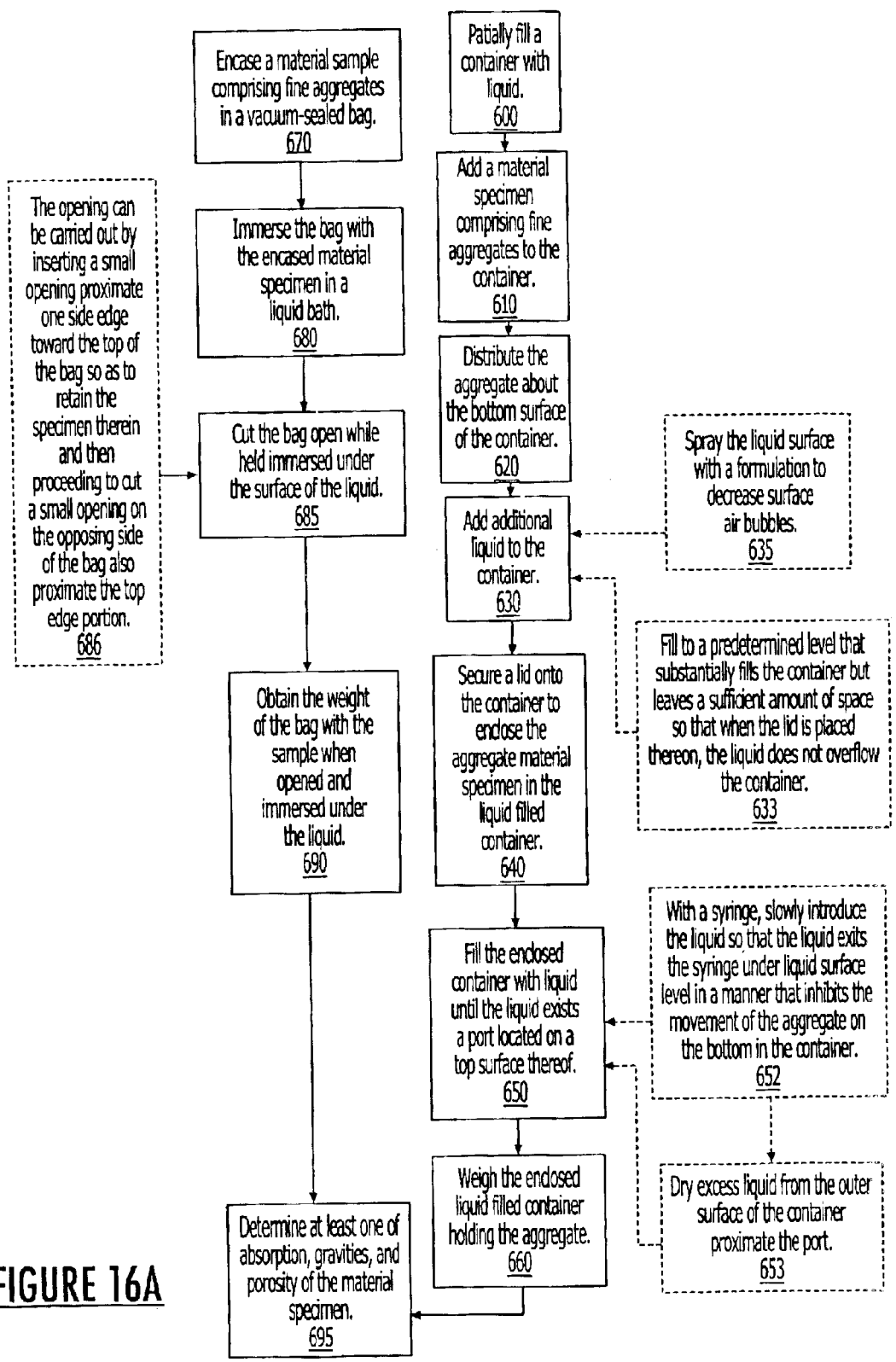
FIG. 16A is a block diagram of operations for carrying out evaluations of material samples according to embodiments of the present invention.
Figure 16B:
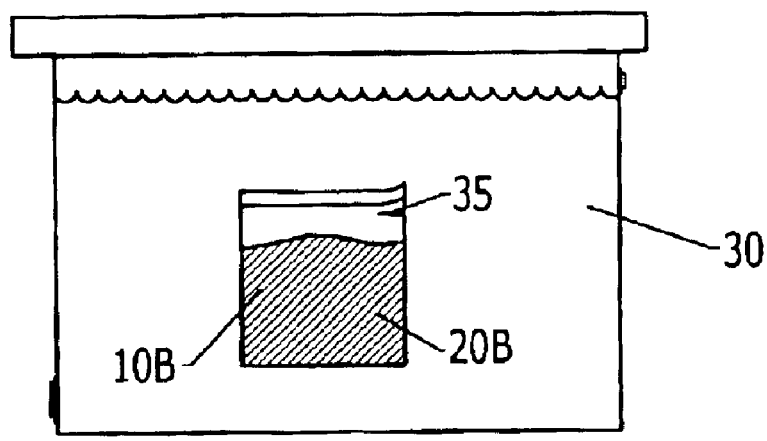
FIG. 16B is a front view of a cut location for a vacuum-sealed bag used to encase a material specimen according to embodiments of the present invention.

For fine aggregates, the opening(s) can be sized to be about 1 inch or less and can be introduced at an upper edge portion as shown in FIG. 16B. A first opening can be introduced and, after liquid enters the bag 20B, another opening about the same size and same position relative to the top can be cut into the bag. For coarse aggregates, as shown in FIG. 18B, a larger opening may be used, such as about 3–4 inches, again in the top edge portion of the bag 20B. Where an inner bag is used, care should also be taken to open both the inner and outer bags (while held immersed in the liquid) so that water or liquid can flow into both. The cut bag(s) 20B can remain immersed for a period of time (such as between about 5–30 minutes and typically about 10 minutes for fine aggregates and about 20 minutes for coarse aggregates) before a weight reading is obtained. In operation, the bags are cut open while they are held immersed or submerged. To obtain the weight, the opened bags and aggregate can be placed on a weighing basket remaining completely submerged. Examples of the submerged or immersed cut bags are shown in FIGS. 16B and 18B.

The aggregate sample 10B may be gently shaken or agitated to facilitate the removal of any remaining air bubbles adhering to the surface of the bag. In any event, the weight of the sample 10B in the opened (previously evacuated and sealed) bag 20B is measured as the bag and sample are held under water.

The measured weights can be input into a general purpose or special purpose processor, and computer program products and algorithms can calculate the percent absorption, apparent specific gravity and bulk specific gravity in a relatively short analysis period (the entire procedure can be carried out in about 10–40 minutes not including the drying period). The calculations will be discussed further below.

Figure 8:
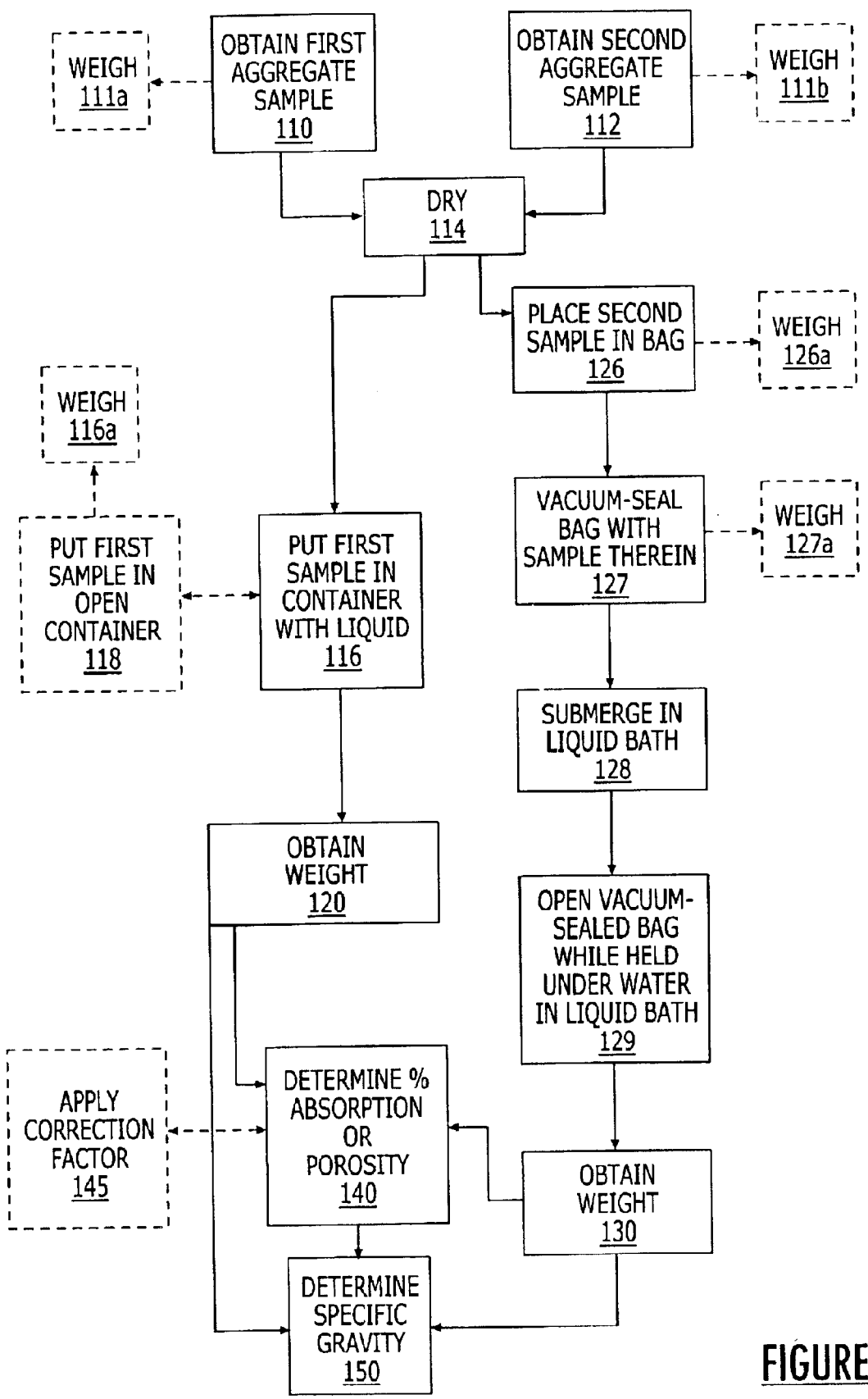
FIG. 8 is a block diagram of a method for determining the percent absorption of aggregate material samples according to embodiments of the present invention.

FIG. 8 illustrates method steps that can be used to obtain the absorption characteristic of aggregate material mixtures according to embodiments of the present invention. First and second aggregate samples are obtained (Blocks 110, 112). The samples can be weighed (and/or the weight can be calculated by subtracting the bag weight from the combined weight of the container and the sample) (Blocks 111a, 111b). The dotted lines in FIG. 8 represents that the associated step is optional. The first and second samples are dried (Block 114). The first and second samples can be dried either before or after they are separated into two different samples (such as in bulk form together after the aggregates are selected from the mixture). The first sample is placed into a container with liquid (Block 116).

In certain embodiments, the first sample can be placed in an open (i.e., not sealed) subcontainer before it is put into the container with liquid and weighed (Block 118), and if so, the subcontainer with the sample can then be weighed while held submerged under liquid (Block 116a). In certain embodiments, additional liquid can be added to the container so as to occupy a predetermined volume.

In other embodiments, the first sample and container are submerged into a liquid bath and liquid or water is allowed to enter therein at atmospheric pressure. In each case, the weight of the first sample and the container is obtained while the sample is submerged (Block 120). As noted above, the same sample can be used for each of the first and second samples. For example, after the sample is dried and analyzed according to one of the first and second samples, it can then be redried and used to obtain the second set of measurements.

The second sample is placed into a bag (Block 126). The second sample and bag can be weighed (Block 126a) before the bag is closed and vacuum-sealed (Block 127). The vacuum seal process can be carried out at approximately 29.7 in Hg. The weight of the vacuum-sealed bag with the second sample can be obtained (Block 127a). The sealed bag is then submerged or immersed into the liquid bath (Block 128). The sealed bag is opened (such as by cutting or puncturing the bag) while the bag and the second sample are held under water (or other liquid) in the liquid bath (Block 129). The weight of the opened vacuum-sealed bag and second sample is obtained as they are held submerged in the water of the liquid bath (Block 130). The percent absorption or porosity can be determined based on the weights of the two samples which have been obtained (Block 140). A correction factor may be applied for highly absorptive aggregate materials (Block 145). The specific gravity may also be calculated (Block 150).

The weight measurement of the dry weight of the second sample and the saturated submerged weight (after the bag is opened under water and weighed, Block 130) can be used to calculate a fully saturated density, $\rho$, (apparent density), of the aggregate sample undergoing evaluation. A second density can be obtained by establishing the weight of the first sample and the weight of the first sample in the container when the sample is completely wetted. The second density can be obtained by obtaining the weight of the volumetric container holding the sample and liquid that are filled to occupy a specific or predetermined volume. This measurement can, in turn, be used to obtain the volume of the first sample. In other embodiments, the wet sample and container in the liquid bath can be placed on top of a scale to obtain the weight under water. The submerged weight and the dry weight or the determination of the volume of the sample and the weight of the first sample allows for the calculation of the second density, $\rho_u$. The following equations can be used to express these density values based on the measurements and relationships (as shown in FIG. 10A).

$$\rho_u = \frac{Col(1)}{Col(1) + Col(2) - Col(3) - \frac{Col(2)}{0.891}} \quad \text{Equation (1)}$$

$$\rho_v = \frac{Col(4)}{Col(4) + Col(5) - Col(6) - \frac{Col(5)}{0.891}} \quad \text{Equation (2)}$$

The container holding the second sample as well as the container holding the first sample may both be weighed before the respective samples are positioned therein, and the weights recorded for use in subsequent calculations of the absorption and/or specific gravity.

For substantially rigid or constant volume container evaluations (such as shown in FIG. 14A et seq.), the following relationships can be used, where the weight of the dry sample A in air is "A" (col. A in FIG. 10B worksheet), and the weight of sample A in container (with lid) filled with water is Waf (col. B in FIG. 10B worksheet), the weight of container (with lid) with water alone filled to the predetermined volume is Wv (top row of FIG. 10B worksheet, volumetric container calibration data), the weight of the dry sample B in air is "B" (FIG. 10B, col. D), and the weight of the bag is Wc (FIG. 10B, col. C), the dry weight of the vacuum-sealed bag with sample B is Wbs, and the weight of the sealed sample B open in water is We (FIG. 10B, col. E).

$$\rho_u = \frac{A}{Wv - (Waf - A)} \quad \text{Equation (3)}$$

$$\rho_v = \frac{B}{Wbs - We - Wc/0.891} \quad \text{Equation (4)}$$

Absorption can be expressed as function of, and may be calculated from, the first and second density measurements. Knowing the absorption and the saturated density one can calculate the SSD condition, bulk specific gravity at SSD, and bulk specific gravity dry basis of the aggregates from established equations. The following equations can be used for these calculations.

$$\% \text{ absorption} = \% \text{ abs} = \frac{100 \, (B - A)}{A} \quad \text{Equation (5)}$$

Apparent Specific Gravity=Saturated Maximum Gravity

Apparent Specific Gravity = $\quad$ Equation (6)

$$\text{Saturated Maximum Gravity} = \rho_v = \frac{A}{A - C}$$

Bulk Specific Gravity, SSD Basis $$\text{Bulk Specific Gravity, SSD Basis} = \frac{B}{B - C} \quad \text{Equation (7)}$$

Bulk Specific Gravity, dry Basis $$\text{Bulk Specific Gravity, dry Basis} = Bsg \frac{A}{B - C} \quad \text{Equation (8)}$$

where:
A=Mass of oven-dry sample in air, g;
B=Mass of saturated surface-dry sample in air, g; and
C=Mass of saturated sample in water, g.

From the two density measurements obtained as described above for the first and second samples, the percent absorption and apparent density can be calculated based on the following calculations.

Generally stated, the measurement(s) associated with the first sample above, where the container is not vacuum-sealed, can be an indication of the density of the dry material where the volume includes the volume of the water permeable voids.

The measurement(s) associated with the second sample above, where the aggregate in the sealed evacuated bag is opened under water, can be a measure of the density of the dry material to the volume of the aggregate excluding the water permeable voids. Therefore, the calculation of absorption (or porosity) from these two quantities can be represented in equation (9) below:

$$\text{Abs \%} = \left(\frac{\rho_v - \rho_U}{\rho_v \rho_U}\right) \rho_{wat} \times 100 \quad \text{Equation (9)}$$

where Abs % is the percent absorption, $\rho_u$ is the density of aggregate simply measured by (a) using the rigid volumetric container and weighing as described herein or (b) by using the value obtained by immersing and weighing the first sample in water. $\rho_v$ is the density (apparent density) of aggregate sealed in an evacuated bag, opened and weighed under water, $\rho_{wat}$ is the density of water (typically about 1 g/cm$^3$).

This method assumes that the density measurement under atmospheric pressure (taken with the unsealed sample) only fills the air voids between aggregates. However, in operation, some water may be absorbed while the sample is being wetted and measured under water. The amount of water absorbed during the density measurements of the unsealed sample will depend on the absorption characteristics of the aggregates being tested. For this reason a calibration is performed for each aggregate type to determine the correction to the final absorption calculation.

A calibration offset or adjustment may be performed on the aggregate in question to correct for the amount of absorption during the determination of density, $\rho_u$. This correction factor or adjustment can be applied to the abs % calculated in equation (9).

The applicable correction adjustment for the aggregate can be determined by examining the amount of absorption as a function of time over which the aggregate is exposed to vacuum. As the operating time of the vacuum process is reduced, the vacuum level achieved within the chamber is reduced. By reducing the vacuum level, the water will not infiltrate the aggregate pores as effectively as under high vacuum. Calibrations can be performed at multiple vacuum time settings to determine the absorption correction to be applied to measurements at atmospheric pressure, when the aggregate is exposed to water for short period of time. Notably, these relationships can also be stated in terms of the actual vacuum setting instead of time. In addition, the initial absorption may be determined by comparing the values obtained using the methods described above to another independent method of measurement.

Figure 9A:
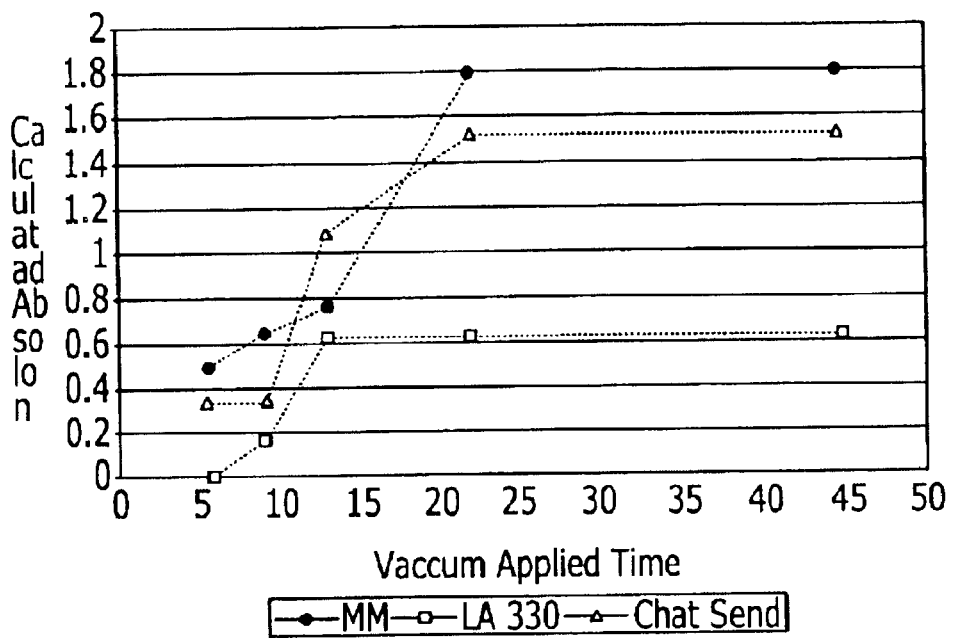
FIG. 9A is a graph of calculated absorption versus applied vacuum time for three different aggregates according to embodiments of the present invention.

Testing represented in the graph in FIG. 9A was performed on three different types of aggregate, two of which were highly absorptive and one of which was a low absorption material. Both the Chat Sand (natural sand from Chattanooga, Tenn.) and the MM aggregate (sand aggregates obtained from the Martin Marietta, Co., located in Raleigh, N.C.) are higher absorptive materials (the MM can also be described as limestone screening); the LA #30 (fine sand particles generally used for concrete mixing) is a lower absorptive aggregate.

A functional representation may be found which will best fit the data shown in the plots of FIG. 9A. The equation may be in the form shown below:

$$\text{Abs \%} = a_c + b\exp(-(t-t_c)^2/\sigma) \cdot f(t) + g(t) \quad \text{Equation (10)}$$

where $a_c$ is the correction applied to the measured absorption in equation (9), and b, $\sigma$, and $t_c$ are fitting parameters, "t" is vacuum time, and f(t) and g(t) are fitting functions.

Figure 9B:
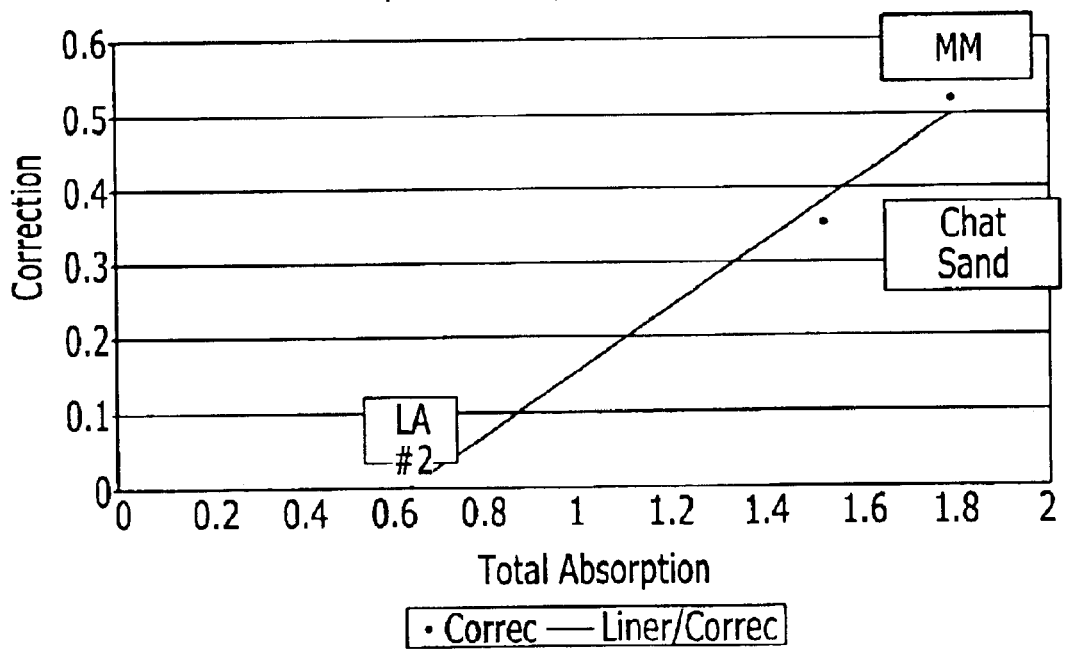
FIG. 9B is a graph of correction values, at zero vacuum, versus total absorption for three exemplary materials based on vacuum time for aggregates with varying absorption characteristics according to embodiments of the present invention.

In other embodiments, another methodology can be used to establish the above relationship for many different samples of aggregates with varying absorption characteristics. This relationship (which can be described as a master relationship) can be established at a factory or a central laboratory at the customer site. Based on this vacuum time, a correlation can be established for determination of absorption correction at zero vacuum. Aggregates of different absorption can be plotted as a function of applied correction versus measured absorption at a given vacuum time. The graph in FIG. 9B shows a representative linear relationship for absorption correction vs. total absorption from a master relationship for maximum vacuum time setting for three different materials. This relationship can also be non-linear and can be performed at other vacuum levels and/or times.

In other embodiments, the correction may be determined by comparing the absorption obtained in the method described above to other values obtained in other independent methods. For example, conducting the above procedure(s) with materials of known composition and/or absorption. The difference between the measured quantity obtained using one of the evaluation methods described above can be compared to the actual known quantity to give the correction factor(s). These factors can be calculated at several known absorption values and a predictive relationship established which can be used in computer-based computation to generate correction factors at different material absorption values. Although described in connection with evaluating absorption, porosity or permeability values can also be obtained similarly.

Once the percent absorption and apparent density are calculated or a relationship established, equations (3) and (4) can be rearranged to calculate B, and C, respectively.

$$B = \left(\frac{(\% \text{ abs})(A)}{100}\right) + A \quad \text{Equation (11)}$$

$$C = A - \left(\frac{A}{\rho_v}\right) \quad \text{Equation (12)}$$

The values for B and C can now be used to calculate Bulk Specific Gravity at SSD (Bsg SSD) and Bulk Specific Gravity dry basis (Bsg) from equation (5) and (6).

Figure 11:
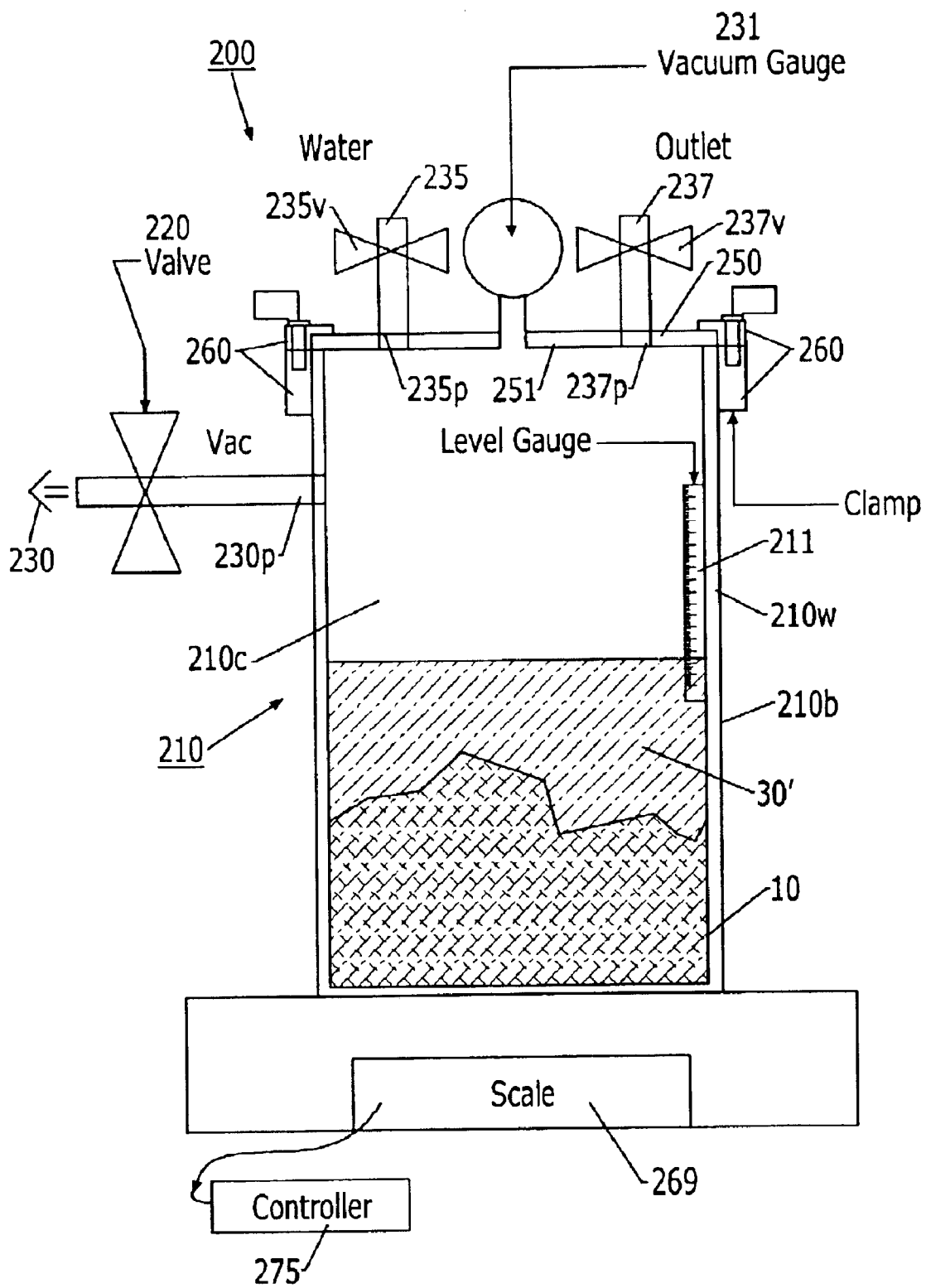
FIG. 11 is a schematic illustration of a system for evaluating apparent specific gravity or density of a material sample according to one embodiment of the present invention.

FIG. 11 illustrates another embodiment of the present invention. Generally stated, in this embodiment, the apparent specific gravity and/or absorption of construction materials (loose or compacted) as discussed previously, can be calculated using weights of a known volume container at various process points (empty and filled with a material sample and liquid after evacuation) and with a quantity of a material sample to calculate apparent density. These methods and systems can assess the filled and empty weights of a volumetrically calibrated container 210.

As shown, the measurement system 200 includes the container 210 which can be sealed. The container 210 includes a volume or level indicator means so that the level of fluid therein can be assessed. As shown, measurement indicia such as a graduated scale 211 can be positioned on a wall 210w of the container 210 so that the level of fluid can be visually monitored. Alternatively, a level marker can be positioned on the wall, or a plurality of level markers (which can be color coded markers) can be used to identify the appropriate level for each type or quantity of sample undergoing evaluation, if different levels are desired. In certain of the embodiments, the container is translucent or transparent so that the level can be readily observed from the outside of the container 210. Other level indicator means or monitors can alternatively or additionally be used such as, but not limited to, infrared sensors, float gauges, and the like.

The container 200 includes a vacuum port 230p and valve 220 in fluid communication with a vacuum source 230, and a vacuum gauge 231. The container 200 also includes a fluid inlet path 235 and outlet path 237, each operably associated with a valve 235v, 237v to control the opening and closing of the paths 235, 237. The container 210 also includes a releasable portion 250 to allow a quantity of a material sample to be positioned in the calibrated container 200. As shown, the releasable portion 250 can be a top portion 251 which includes a fluid inlet path and outlet path port 235p, 237p, respectively. The top portion 251 can be releasably attached and sealed to the container body 210b. The releasable portion 250 can be attached to the container body 210b in any suitable manner well known to those of skill in the art. For example, the top portion 251 can be sealed and secured to the body 210b via a gasket, O-ring, or other sealant material and a clamping structure 260 as shown in FIG. 11. Alternatively, the releasable portion 250 can be configured to matably attach to or threadably attached to the underlying container body 210b (threads may be provided on the inside or outside of the top portion of the container body). In operation, the releasable portion 250 allows access to the inside of the container 210c. The releasable portion 250 may be otherwise formed into the container 210, such as in a sidewall or bottom portion (not shown). The valves and fluid passages can also be alternatively formed into the container 210.

The system also includes a scale 269 which can be operably associated with a computer or computer processor 275 to automatically relay and record the measured weights at particular process points as desired. Similarly, each of the valves 220, 235v, 237v can be configured to be controlled manually or by automatic controls to open and close at desired process points.

In operation, in this embodiment, the apparent specific gravity can be calculated using the container 210 (shown as a calibrated cylinder). The "calibration" is based on establishing a known volume for the container 210 or cylinder. A weight of the container or cylinder 210 can be obtained with the container in an unfilled/empty condition. Liquid or water 30' can be added to the empty cylinder 210 until it is filled to a desired level. The filled container weight can then be measured. Since the density of water is known as discussed above (i.e., 1 g/cm³) and the weight of the empty cylinder is known, the cylinder volume can be calculated by the following equation:

$$\text{Volume} = \frac{\text{Total Weight} - \text{Empty Cylinder Weight}}{\text{Density of Water}} \quad \text{Equation (13)}$$

In this embodiment, the releaseable portion 250 can be released such that a known amount of dry material sample 10 can be added to the container 210. The releaseable portion 250 (or lid) is then replaced (shown as residing on top of the cylinder) and secured or locked in position. A vacuum (with the vacuum valve 220 open) is then pulled on the container 210. The vacuum gauge 231 can be used to indicate when a proper or desired vacuum level has been established in the container 210. In certain embodiments, a vacuum level of about 29.7 inches Hg is suitable. Once the desired vacuum is achieved within the container 210, the vacuum valve 220 is closed and the water inlet valve 235v is opened to allow water 30' to enter into the inlet port 235p and into the container 210. A water level gauge 211 can be used to monitor the water level 30'. As noted above, a transparent or translucent walled container can also be used to visually monitor the water level inside the container.

In any event, once the level of water 30' is above the sample 10, the outlet valve 237v can be opened to allow the water to flow out of the container 210 as desired (typically associated with methods desiring to fill the entire container volume with water). When the container 210 has the desired level of liquid or water therein, the weight of the sample plus water can be used to calculate the maximum density (apparent density) of the sample. In certain embodiments, it may be preferred to fill the container with the water to obtain the filled weight. However, other levels can also be used as long as their volumetric weights can be reliably determined/established for input/adjustment to the mathematical relationships and calculations noted below.

$$V_S = V_C - \frac{WT - WS}{WD} \quad \text{Equation (14)}$$

$$\text{Apparent Density} = \frac{WS}{V_S} \quad \text{Equation (15)}$$

Where:
Vs=volume of sample
Vc=Calibrated volume of the cylinder
WT=Weight of sample plus water in the cylinder
WS=Weight of (dry) sample
WD=Density of water, generally 1 g/cm³ Once the container 210 with the sample 10 has been subjected to vacuum and filled with water, the density can also be calculated by the water displacement method. In order to calculate density, the weight of the dry sample 10 in air and the weight of the sample 10 and container 210 submerged under water in a conventional liquid bath can be determined. Using a correction factor or value corresponding to the offset in weight for the submerged volume of the cylinder (such as described for other embodiments above), the apparent density can be calculated by using the measurements obtained as described above.

The process explained above can be fully automated with computer controls and appropriate sensors to monitor water level, vacuum level and valve shut off mechanism. It can also automatically monitor weights from the scale 269 and relay the measurement data to a controller 275 so that computer program products can automatically relay the weights from the scale 269 and perform the calculations and output or display the results without relying on operator input.

Figure 12:
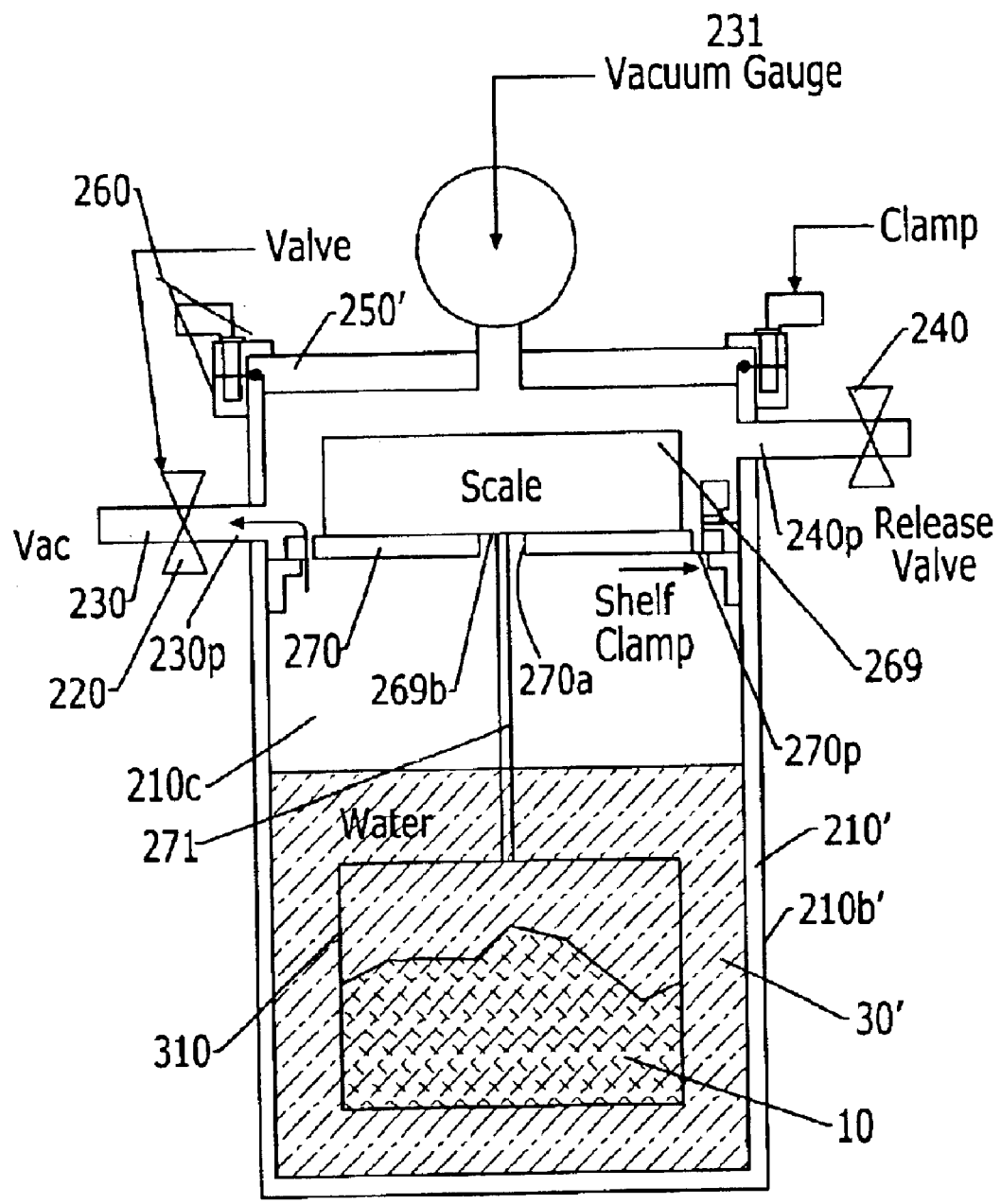
FIG. 12 is a schematic illustration of a system for evaluating material properties such as apparent specific gravity, density, or absorption of a material sample according to one embodiment of the present invention.

Another embodiment of the invention, as shown for example in FIG. 12, can include an integrated system 300 for determination of the apparent specific gravity and/or the amount of water absorbed by the material. As shown, similar to the embodiment of FIG. 11, the system 300 includes a vacuum gauge 231, a vacuum source 230 and valve 220 operably associated with the vacuum source 230 and the port 230p to the container body 210b'. The system 300 also includes a releaseable portion 250' and sealable attachment means 260 to secure the releaseable portion to the container body 210b'. The scale 269 can be mounted inside the container 210'. The system 300 can also include a release valve 240 and associated port 240p to control the opening and closing of the chamber 210c defined by the inside of the closed container 210 so as to return the chamber to atmospheric condition after it has been exposed to an evacuated state.

In the embodiment shown, vacuum access ports 270p are formed into a mounting shelf 270 that can hold the scale 269 above the material sample 10. The mounting shelf 270 can also be otherwise configured such as in a grate, mesh or foraminated structure. As is also shown, the mounting shelf 270 can be configured to be releaseable from the container body 210b' to allow access to the bottom portion of the container body 210b'. The mounting shelf 270 can also include an aperture 270a formed therein to allow a longitudinally extending suspension member 271 to extend freely from the bottom surface 269b of the scale 269 through the aperture 270a.

The material sample 10 can be held in a subcontainer 310 inside the container 210'. In certain embodiments, the subcontainer 310 is held suspended above the bottom of the container body 210b' in communication with the scale 269. In the embodiment shown, the suspension member 271 extends between the sub-container 310 and the scale 269 and allows the scale 269 to weigh the material sample 10 at the desired process points. The subcontainer 310 is configured to allow water 30' to enter therein when submerged or held immersed in liquid or water 30' in the container 210 and also to retain the material sample 10 therein during the evaluation. For fine aggregates, a subcontainer 310 having a closed bottom and sides (at least up to the material sample level) may be preferred. The subcontainer 310 can include apertures or openings formed into the top portion of the subcontainer 310 to allow the water to enter therein during evaluation. In different embodiments, the subcontainer 310 can be a rigid or collapsible body.

The scale 269, subcontainer 310, and material sample 10 can, thus, be configured to be a part of an integrated assembly, which can be placed within the outer container 210'. The container 210' is sized and configured to hold a sufficient quantity of water to submerge the material sample 10. The system 300 is configured to be sealable in an airtight manner and can be equipped with gaskets and locking mechanisms to allow a sufficient vacuum to be introduced to the chamber 210c.

In operation, a known quantity of dry material sample 10 is placed in the subcontainer 310. Liquid, typically water 30', is introduced into the chamber of the container 210' in a quantity sufficient to hold the subcontainer and sample submerged under the water during evaluation. When the subcontainer and material 10 are completely submerged under water 30', a first weight can be obtained at atmospheric pressure. A vacuum is then applied through the opened vacuum valve 220 attached to the vacuum source 230. After the vacuum has been applied for a specified amount of time or reaches a specified vacuum level (such as about 29.7 in Hg) which can be monitored by the vacuum gauge 231 attached to the container in communication with the chamber 210c, the container chamber 210c can be returned to atmospheric pressure by opening the release valve 240 and closing the vacuum valve 220. A second weight reading can be obtained after the scales stabilize. The scale reading can be continuously or semi-continuously monitored to determine when the stabilization point has been reached.

The second weight ($w_2$)(associated with the weight of the material in water after applying a vacuum) will be higher than the weight of the first measurement ($w_1$) taken before evacuation at atmospheric pressure. Using the weight in water of the first measurement, a first density value can be obtained; using the weight in water of the second measurement, a second density (maximum density or apparent specific gravity) can be obtained. The first density and the second density may be used to calculate the absorption of the material. The table below illustrates the variable identifier used in the mathematical calculations described below.

| Sample | Weight of Dry Material | (First weight) Weight in Water at 1 atm. | (Second weight) Weight in Water After Being Subjected to a Vacuum | First Density | Second Density |
|---|---|---|---|---|---|
| 1 | $W_1$ | $W_2$ | $W_3$ | $\rho_1$ | $\rho_2$ |
| 2 | $W_1'$ | $W_2'$ | $W_3'$ | $\rho_1'$ | $\rho_2'$ |

Equations to calculate the first and second density are given below.

$$\rho_1 = \frac{w_1}{w_1 - w_2}\rho_w \quad \text{Equation (16)}$$

$$\rho_2 = \frac{w_1}{w_1 - w_3}\rho_w \quad \text{Equation (17)}$$

Where $\sigma_w$ is the density of water, usually taken to be 1 g/cm$^3$ and the other variables are described in the table above. These values may then be used to calculate the absorption using the formula given below $$\text{Abs}\% = \left(\frac{\rho_2 - \rho_1}{\rho_1 \rho_2}\right)(100)\rho_w \quad \text{Equation (18)}$$

The above systems and processes can be partially or completely automated with sensors and controls integrated into a computer operated/controlled process for one or more of the determination of weights, calculation of densities and percent absorption.

Figure 13:
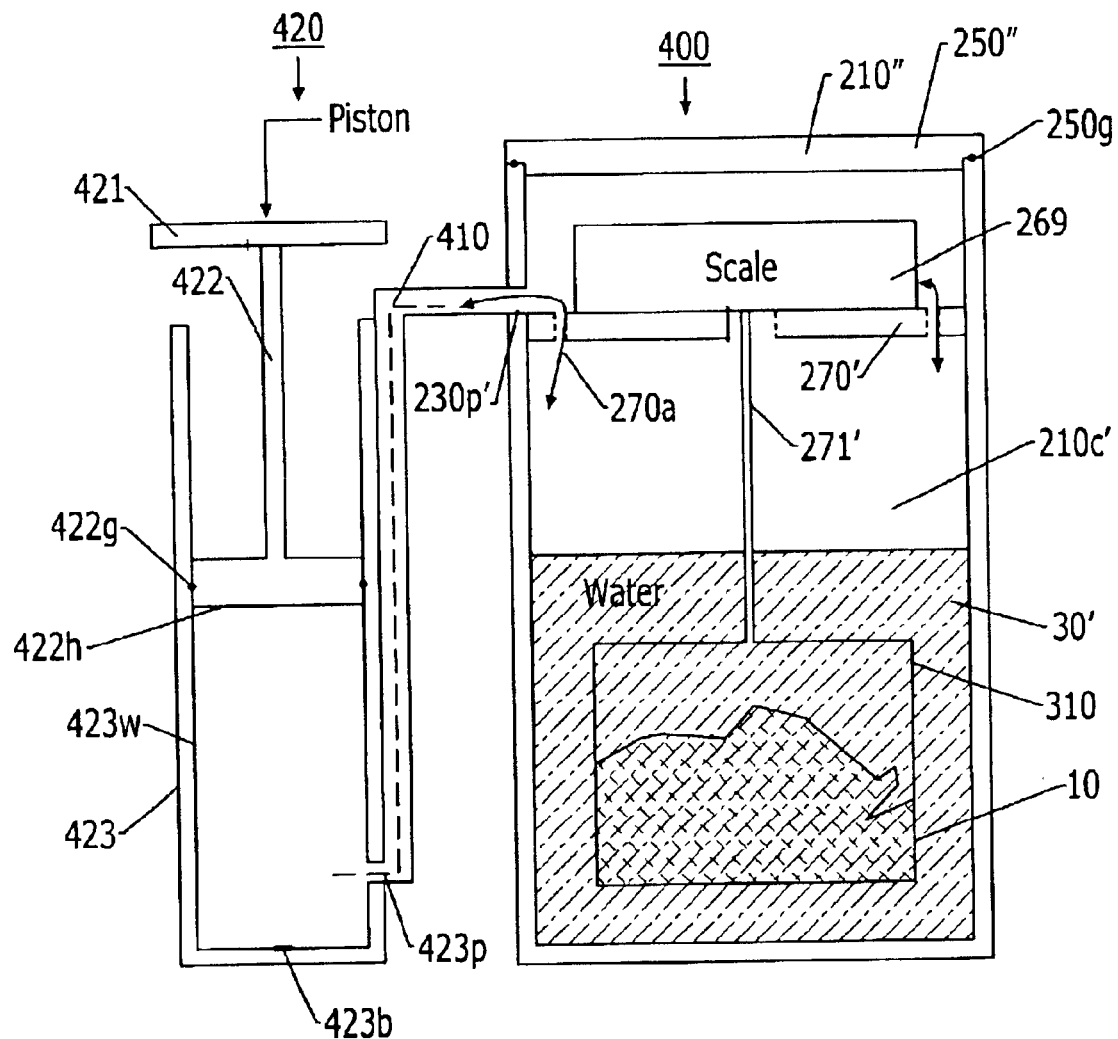
FIG. 13 is a schematic illustration of a system for evaluating material characteristics such as apparent specific gravity, density, or absorption of a material sample according to one embodiment of the present invention.

FIG. 13 illustrates yet another embodiment of the invention that may be used to determine the amount of water absorbed by the material sample 10. This system 400 employs a pressure source 420 (in contrast to a vacuum source). Similar to the embodiment shown in FIG. 12, the scale 269 resides on a mounting shelf 270' in the container 210" above the liquid level 30'. The mounting shelf 270' can be configured with apertures to allow air to flow therethrough and into the chamber 210c' so that the chamber can be pressurized during evaluation. As before, the scale 269 can be operably associated with the material sample 10 that is held in the subcontainer 310. The subcontainer 310 can be suspended below the scale 269 and above the bottom of the container body 210". The scale 269, subcontainer 310, and material sample 10 are all configured to reside in the outer container 210" during evaluation. In operation, the container 210" is sealed and configured to withstand a desired elevated pressure (above atmospheric) pressure which may be applied to the chamber 210c' and the material sample 10.

The container 210" includes a releaseable top portion 250" (shown as a lid) which can be sealed to the container body 210b" such as via a gasket 250g and matable or friction fit connection therebetween. As before, the releaseable portion can be removed or moved to allow access to the chamber 210c'.

The system 400 also includes a pressure source 420 which is in fluid communication with the container chamber 210c'. The container body 210b" includes a pressure port 230p' which allows the pressurized air to move in and out of the chamber 210c'. An enclosed pressure delivery path 410 extends between the pressure port 230p' and the pressure source 420 to direct the pressurized fluid, typically air, into the sealed chamber 210c'. The delivery path 410 can be provided by a conduit, hose, line, pipe, or other suitable structure. In certain embodiments, the pressure source 420 is a piston 421 with a plunger 422 cooperating with and sealably attached to an associated cavity 423. The plunger head 422h can include an O-ring or gasket 422g thereabout to seal the plunger head 422h against the walls of the cavity 423w as the plunger head 422h moves toward and away from the bottom of the cavity 423b. As the plunger 422 moves toward the bottom of the cavity 423b, pressurized air is directed out of the cavity port 423p through the delivery path 410 and into the sealed chamber 210c'.

In operation, water can be put into the container 210" such that the subcontainer 310 and material sample 10 are completely submerged under water. A first weight ($w_1$) can be obtained while the sample 10 and subcontainer 310 are held immersed under water and while the chamber 210c' is at atmospheric pressure, either by having the operator read the scale 269 or by automatically relaying or retrieving the data associated with the scale reading and transmitting it to a computer or controller (not shown). The pressure source 420 can increase the pressure in the chamber 210c'. For example, in certain embodiments, the increase in pressure can be applied by automatically or manually moving the piston 421 to direct pressurized air from the port 423p at the cavity bottom into the delivery path 410 and then into the container 210".

After the pressure has been applied for a specified amount of time or after the pressure in the chamber 210c' reaches a specified pressure level, a second reading ($w_2$) can be obtained from the scale 269, again either manually or via a computer interface. In some embodiments suitable pressures may be in the range of about 1.5–3 atm. In any event, the system 400 is configured to withstand whatever the desired pressure for the particular application.

The pressure can be applied at a constant rate so as to be gradually introduced over a desired evaluation period (corresponding to the container size and the dead volume of the plumbing). The system 400 can include one or more internally mounted pressure gauges/sensors (not shown). Alternatively, the air (or other fluid, preferably gas and more preferably air) can be input into the container 210" until the scale 269 stabilizes (indicating no change in weight and that the water has entered all voids). Continuously or semi-continuously monitoring the scale readings via a controller interface may allow accurate determination of the appropriate time at which to take the second weight reading. Further, the controller can numerically or graphically correlate the time at which the stabilization point (or points) is reached along a time chart and automatically record or correlation to of the stabilization time with the time at which the second weight reading is obtained. The system can be configured to take multiple weights about desired times during the process and average or correlate the readings for analysis. These readings may also be used to provide the second weight value (by taking weight readings at various points in the process, such as at multiple points proximate to reaching a desired stabilization level (with reduced fluctuation in readings) and averaging or correlating the weights. In addition, taking weights during a broader time frame may allow the weights to be compared to a predictive model or to monitor the relative change during the process itself. Each of these may allow an operator to be alerted as to discrepancies in the testing protocol or to the potential that the material is deficit in its properties based on the identified departure from a predictive model or statistical norm or a particular material composition.

Using the weight in water of the first measurement ($w_1$) a first density pi can be obtained, using the weight in water of the second measurement ($w_2$) a second density $\rho_2$ can be obtained. The first density $\rho_1$ and the second density $\rho_2$ may be used to calculate the absorption of the material according to the equations and variable identifications given for the embodiment shown in FIG. 12 (same table and equations). Again noting that $\rho_w$ is the density of water, usually taken to be 1 g/cm$^3$. With these values the absorption may be calculated using the formula given for the FIG. 12 embodiment described above.

Figure 18A:
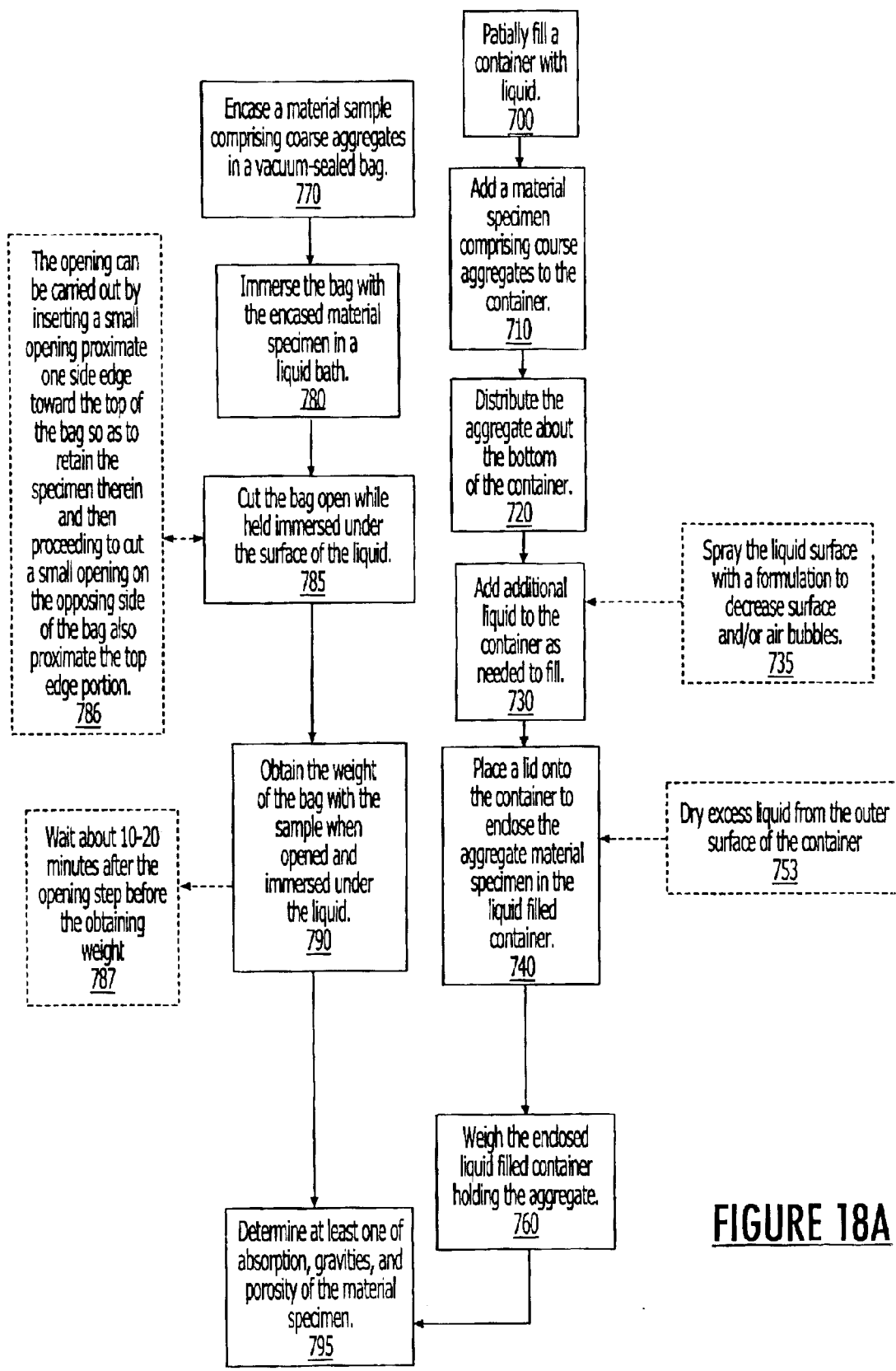
FIG. 18A is a block diagram of operations for carrying out evaluations of material samples according to embodiments of the present invention.
Figure 18B:
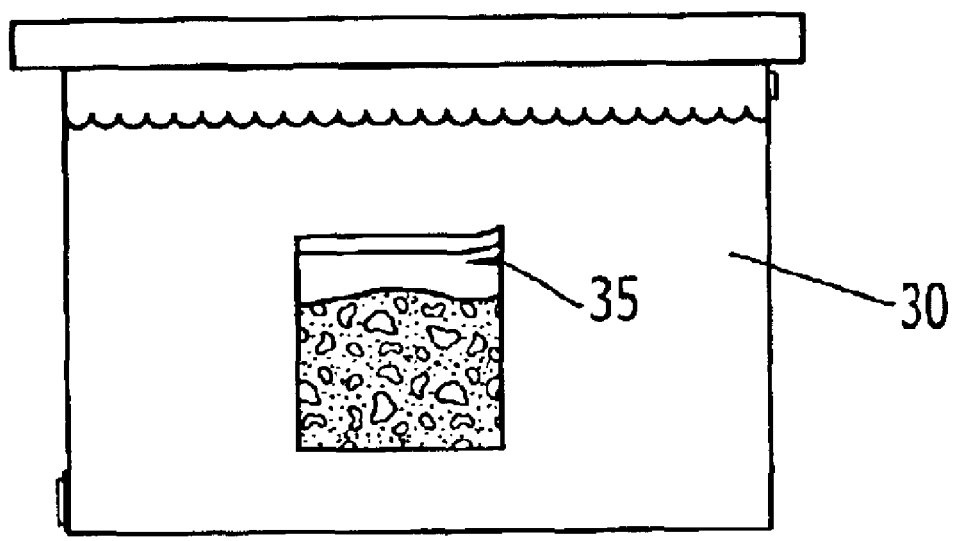
FIG. 18B is a front view of a location of a cut for a vacuum-sealed bag used to encase a material specimen according to embodiments of the present invention.

In still other embodiments, as shown in FIGS. 16A, 18A, and 19 the apparent specific gravity, porosity, permeability or % absorption of aggregates can be determined. The apparent specific gravity and/or % absorption values can be used to determine bulk specific gravity and saturated surface dry (SSD) weight of the material specimen undergoing evaluation. The methods can be used to evaluate both fine and coarse aggregates. For each of these embodiments, a volumetric container calibration procedure can be carried out and this value used in the material property evaluations and/or calculations. The calibration can be run hourly, daily, weekly, or even before each evaluation. The calibration can also be carried out upon change in aggregate source. As described above, the volumetric container 520A, 520A', 820A (FIGS. 14A, 17, 19) is configured to define a consistent internal volume even when the container is filled to capacity with liquid and/or liquid and aggregate mixtures.

In certain particular embodiments for the calibration of the container 520A shown in FIG. 14A, the fixture should be placed on a level surface (the level can be confirmed using a level indicator tool) and then the container placed on the fixture base surface until it aligns with the stops or other mounting position indicators as desired. The water is input to the fill line indicated (not quite full and at about 0.25 inches from the top in the embodiment shown in FIG. 15A), the lid 520L is clamped or secured onto the container 520A, taking care to keep the water level at or below the line to avoid spills as the lid is placed onto the container 520A. The syringe 525 is inserted into port 520p and water is introduced below the water level in an amount sufficient to fill the container and lid volume as demonstrated by the embodiment shown in FIG. 15B. Slow and/or gentle insertion/release of the liquid or water during this step will inhibit air bubble formation inside the container. This operation is continued until the container is full. To verify, an operator or optical reader can monitor the viewing port 521 to determine when water can be seen coming out of, entering, or approaching the top portion of viewing port 521. Other automated sensing means can also be used as is known to those of skill in the art. The excess water can be removed or wiped off the container 520A and the fixture 540. Once full (i.e., the liquid occupies the internal defined volume) the entire fixture 540 with the container 520A and lid 520L that is attached thereto and fixed in place are positioned on a scale and the weight obtained. The lid 520L should be attached with sufficient force so as to resist the urge to float away from the body of the container as the internal volume is occupied with liquid. The weight can be recorded on a physical worksheet or record or electronically input into a computer. The steps in this paragraph can be repeated a plurality of times (such as three) and the weights can be averaged. However, if the variation between the calibration weights is larger than about 1 gram, and typically if the weights vary by about 0.2–0.5 grams, then there may be a problem with either the fixture, the container, or the procedure as it is being carried out.

A similar calibration procedure can be carried out for the container 520A' shown in FIG. 17 (or that shown in FIG. 19). In this embodiment, the container 520A' can be filled with liquid (typically water) so that the liquid level is substantially at the top of the bowl. As before, the container 520A' should be placed on a level surface. The lid 520L' can be placed on the container 520A' by aligning and gently pressing the lid down onto the underlying container so that liquid flows from the lid port 520p'. The lid 520L' should be arranged so that it engages and seats with the underlying upwardly extending sides of the container 520A'. External clamps are not required. Rather, the lid and container can be configured to mate or attach in a number of ways so that, in position, the lid 520L' remains on the container and the internal volume remains constant even when liquid fully occupies the internal volume and is pressing up against the lid. As before, the excess liquid can be removed from the outside of the container and attached lid. When properly seated, liquid should not exit the side mating regions (i.e., joint) between the container and lid. The liquid filled container can be placed on a scale and the weight obtained. This procedure can be repeated a plurality of times and the weights averaged. FIG. 10B illustrates that three weights can be obtained and recorded onto a worksheet. As described for the calibration procedure above, the calibration procedure can be periodically repeated.

Referring again to FIG. 16A, a sufficient quantity of a material sample comprising fine aggregates is oven-dried and separated into two material samples 10A, 10B, each comprising fine aggregates. In particular embodiments, a single test can be performed based on a 2000 gram sample split into two samples of 1000 grams. Sample A is evaluated according to the operations illustrated in Blocks 600–660, while sample B is evaluated according to the operations illustrated in Blocks 670–695.

A container (such as the volumetric container 520A shown in FIG. 14A) can be completely dried (inside and out). In certain embodiments, the Sample A evaluation operations in Blocks 610–660 are carried out rapidly in under about 2–3 minutes, and typically in under about 2 minutes. Increased evaluation time may impact the absorption determination.

The container can be placed into the fixture and so that it is in its proper location (resting against stops as desired). The container is partially filled with liquid (Block 600) and a material specimen comprising fine aggregates (Sample A) is added to the container (Block 610). Typically the operation in Block 600 is performed first before the operation described in Block 610, but may be performed in reverse order in certain applications. In certain embodiments, about 500 ml of 78° F. water is put into the container. The weight of the dry sample A can be obtained (and it can be in a size to be about 1000 +/−1 gram). This value can be recorded in Col. A of the worksheet shown in FIG. 10B.

The aggregate sample is distributed about the bottom surface of the container (Block 620). This operation can be carried out by using an implement such as an aluminum spatula or other device to stir the aggregate to spread the aggregate so as to be substantially equally distributed in the bottom of the container. The spatula can be gently inserted into the container to contact the bottom of the container proximate the wall perimeter or outer circumference. The spatula can be slowly and gently dragged from the outer perimeter toward the center of the container. The spatula can be raised and directed to a circumferentially spaced apart location and the stirring motion repeated. Typically, the distribution procedure is carried out at about 4–10 equally spaced locations about the circumference to return to the starting location.

Additional liquid is added to the container (Block 630). The liquid can be added to a pre-marked liquid level line in the container or a particular volume of liquid can be added. The former allows for variation in the material sample size. Typically, the liquid is added to be about 0.25 inches from the top of the container. The liquid should be kept at a sufficient distance below the surface to avoid spills during lid placement (Block 633). The liquid surface can be spared with a substance or formulation to decrease or remove surface or air bubbles (Block 635). In certain embodiments, a spray bottle of isopropryl (rubbing) alcohol can be used to spray the top of the liquid with the substance to remove or eliminate surface bubbles. As noted above, other suitable substances may also be used.

A lid is secured to the container to enclose the aggregate material in the liquid (Block 640). Together, the lid and container define a fixed internal (constant) volume. In certain embodiments, the lid can be clamped onto the container body. The enclosed container is then filled with liquid until liquid exits a port (or neck opening) located on a top surface thereof (Block 650). The enclosed liquid-filled container holding the aggregate is then weighed (Block 660). This weight may be recorded in Col. B of the worksheet illustrated in FIG. 10B.

In particular embodiments, the fixture is weighed with the enclosed liquid-filled container. In certain embodiments, a syringe can be used to slowly introduce the liquid so that the liquid exits the syringe under the liquid surface level in a manner that inhibits movement of the aggregate on the bottom of the container (Block 652). Excess moisture can be dried from the outer surface of the container proximate the port (Block 653). If liquid seeps from the rim of the container (i.e., the joint between the lid and container), this liquid should not be removed, and should be allowed to remain on the container during the weighing process.

The operations in the left column will now be described (for sample B). They can be carried out prior to, subsequent to, or concurrently with those in the right column described above.

Dried sample A of fine aggregates can be encased in a vacuum-sealed bag (Block 670). As noted above, a Corelok® vacuum apparatus and associated bags and equipment can be obtained from InstroTek, located in Raleigh, N.C. Additional description of a suitable seal/evacuation procedure is provided in co-assigned U.S. patent application Ser. No. 09/580,792, the contents of which are incorporated by reference herein. In certain embodiments, three spacer blocks can be positioned in the vacuum chamber to help support the specimen during seal/evacuation. As for sample A, sample B can be weighed prior to insertion into the bag to obtain the weight (typically about 1000 grams +/−1 gram) of the sample for evaluation. The weight can be recorded in Col. C of the worksheet shown in FIG. 10B. The bag can also be weighed and its weight recorded in Col. C. The bag and sample can be placed in the vacuum chamber. The sample can be distributed inside the bag. The bag can be folded about one inch about its open end and held to shake the aggregate sample from side to side without loosing material from the bag. The sample should be substantially flat inside the bag. Piling of aggregate may restrict airflow from the bag during the evacuation procedure. The open side of the bag can be laid over the sealing bar and the vacuum chamber door closed. The vacuum apparatus can be set to run on a pre-selected program (such as vacuum level of about 99% of absolute vacuum and a seal temperature and associated dwell time). When handling the bag and sample, care should be taken to maintain the integrity of the bag and/or seal.

The vacuum-sealed encased sample can be removed from the vacuum apparatus and placed in a liquid bath for liquid (typically water) displacement analysis. The bag encased material specimen can be immersed into the liquid bath (Block 680) and the bag cut open while the bag is held immersed in the liquid bath (Block 685). The bag should be held under the liquid while opening; air introduced into the bag may influence the results. The operator may use fingers or other implements to force the bag to open at the cut to allow liquid to freely flow into the bag. The opening can be propped open for about 45 seconds an any small residual air bubbles allowed to escape from the bag. The cut can be a relatively small cut inserted proximate one side of the bag, about a top edge portion, and can be introduced into the bag so as to retain the specimen therein. Subsequently, after water or liquid has substantially filled the bag, another opening can be cut on the opposing side of the bag also proximate the top edge portion (Block 686). The opening can be sized at about 0.5–1.5 inches and is typically about 1–1.5 inches in width. FIG. 16B illustrates a suitable location for the opening. Any residual air bubbles that may be formed proximate to the cut openings can be squeezed out by having the operator press against these regions. After the air bubbles are removed, the open bag can be placed on a platform under water, the platform being operably associated with a scale. The open end of the bag can be oriented upward to allow water to freely enter therein. In other embodiments, the bag can be placed on the platform (that is adapted to be in communication with a scale) under water prior to opening the bag or the platform can be lowered in the bath into proper location without moving and/or lifting the bag itself.

In any event, the weight of the bag with the sample, when opened and immersed under the liquid in the liquid bath, is obtained (Block 690). The bag and/or sample should not contact the side(s) or bottom of the liquid bath container while the weight is obtained. In particular embodiments, the sample can stay in the liquid bath for a period of time before the weight is obtained, for example, about 5–15 minutes, and typically about 10 minutes. The submerged weight can be recorded in Col. E of the worksheet shown in FIG. 10B. At least one of the % absorption, specific gravities, and porosity can be determined based on the measurements obtained (Block 695). As before, the recorded values can be input into the computer and the computer can be directed to run a pre-selected program to carry out the desired calculations/evaluations, including, for example, apparent density, percent absorption, bulk specific gravity (SSD), and bulk specific gravity (Bsg).

Referring to FIG. 18A, operations of a similar procedure are illustrated, this procedure being directed to analyzing coarse aggregate samples. As before, a sufficient quantity of a material sample comprising coarse aggregates is oven-dried and separated into at least two material samples 10A, 10B, each comprising coarse aggregates. In particular embodiments, the quantity of aggregate used to carry out this test may be about twice the amount specified in ASTM C 127 rounded up to the nearest multiple of 4000 grams (for example, a sample undergoing evaluation having a maximum aggregate size of 19 mm requires a sample size of about 3 kg). For this test, the 3 kg is doubled to 6 kg and the nearest multiple of 4 kg (rounded up) is 8 kg. In this example, a single test uses 2 kg. In certain embodiments, four separate tests, each using 2 kg are run, two for sample A and two for sample B.

At least one of the sample A specimens is evaluated according to the operations illustrated in Blocks 700–760, while at least one of the sample B specimens is evaluated according to the operations illustrated in Blocks 770–790.

A rigid container (such as the volumetric container 520A' shown in FIG. 17) can be completely dried (inside and out). In certain embodiments, the Sample A evaluation operations in Blocks 710–760 are carried out rapidly in under about 2–3 minutes, and typically in under about 2 minutes. Increased evaluation time may impact the absorption determination.

As shown in FIG. 18A, the container can be partially filled with liquid (Block 700). Typically, the container is filled about half way with water at about 78° F. The sample of coarse aggregates can be added to the container (Block 710). As before, the container can be partially filled with water before the aggregate is added. In other embodiments, the water or liquid is added after the aggregate is in the container. In any event, the aggregate can be distributed so that it is substantially evenly located over the bottom portion of the container (Block 720). There should be sufficient liquid to cover the aggregate in the container. Because the aggregate sample comprises coarse aggregate, a rubber mallet or other blunt object can be used to impart shock waves into the water by hitting the mallet against the outer wall of the container at various positions low on the container wall (such as hitting the wall twice at four places spaced at about 90 degree increments) about the perimeter thereof to facilitate the even distribution of the sample and/or to dislodge air bubbles. Other distribution or air dissipation methods can also be used, but care should be taken to keep the aggregate immersed.

Additional liquid can be added to the container as needed to substantially fill the volume (Block 730). The surface of the liquid can be sprayed with a liquid to decrease or eliminate surface bubbles (Block 735). The lid can be placed onto the container to enclose the aggregate and liquid in the container (Block 740). Properly seated and filled, some liquid will spill out when the lid is engaged with the container. Liquid may be needed to be added in certain embodiments (such as if the liquid does not exit the port 520p' of the container shown in FIG. 17 or if the liquid is below the level of the fill line 820f in the embodiment shown in FIG. 19). This excess liquid on the exterior of the container/lid can be dried. The enclosed container with the liquid/aggregate can be weighed (Block 760). This value can be recorded in Col. B of the worksheet shown in FIG. 10B.

Similar to the embodiment described for FIG. 16A, sample B can be encased in a vacuum-sealed bag (Block 770). The bag can be weighed and the weight recorded in Col. C of the worksheet shown in FIG. 10B. In certain embodiments an inner bag is used with the outer bag to hold the coarse aggregate sample. Both weights can be obtained together. The sample B weight can be obtained and recorded in Col. D (typically about 2000 g+/−1 gram. The sample can be placed in the inner bag. Where the inner bag comprises air channels, this surface feature may present a rough or coarse texture defining air channels (to facilitate air removal during evacuation), this side may be oriented to be down where the bulk of the weight of the sample can rest during the evacuation procedure. The weight of the sample in the bag should be supported on a support surface such as a table when filling and handling to protect against punctures. The inner bag and sample can be inserted into the outer sealant bag and then placed into the vacuum chamber. The sample can be spread (typically by hand) so as to be substantially evenly distributed about the surface of the chamber in the bag(s).

As before, the encased material specimen is immersed in a liquid bath (Block 780), and the bag is cut open while it is immersed in the liquid (Block 785). The opening can be propped open a sufficient distance to allow liquid/water to freely enter therein. Any residual air bubbles can be allowed to escape. Although not individually sealed, access to the inner bag can be had via the cut and the inner bag can also be propped open too to allow the water to enter therein. The opening can be a cut inserted into one upper corner of the bag (see FIG. 18B). The opening can be a relatively small opening introduced in one side with a size of about 3–4 inches. A second opening of similar size and position can then be introduced into the other side (Block 786). The second opening may be introduced after water has substantially filled in the bag. Any excess air/vapor can be squeezed out of the upper corners of the bag by running fingers across the top of the bag and forcing the gas out of the cut openings.

As before, the aggregate-filled bag can be placed on a platform (operably associated with a scale) under water/liquid. The bag can be folded to place it on the platform; however, once on the platform, it can be unfolded under liquid (water), to allow the liquid to freely flow into the bag. The weight of the opened bag under water with the sample can be obtained (Block 790). The weight may be obtained after waiting about 10–20 minutes after opening the bag. The bag and/or sample should not contact the bottom sides or float out of the liquid bath tank during the weighing measurement. The submerged weight can be obtained and recorded in Col. E of the worksheet shown in FIG. 10B. If the aggregate size is such that more than 2000 grams need to be evaluated, both columns of operations for an additional sample A and sample B should be repeated. At least one material parameter or characteristic of the aggregate is determined such as one of specific gravities, absorption, and porosity (Block 795). The weights can be input into the computer by the operator (or automatically by upload from electronic scales) and the operator can run a pre-selected program to provide the desired evaluation and/or determination. The Aggplus™ System and/or AggSpec™ computer program is available from InstroTek, of Raleigh, N.C.

Other embodiments of the invention anticipate that similar calculations to those described herein can be made to assess material permeability, porosity, asphalt absorption, maximum density, maximum specific gravity, and the like. Further, the methods can be fully or partially automated. Additional details of each of these embodiments are described in co-pending and co-assigned U.S. patent application Ser. No. 09/580,792 the contents of which are hereby incorporated by reference as if recited in full herein The invention will now be illustrated with reference to certain examples which are included herein for the purposes of illustration only, and which are not intended to be limiting of the invention.

EXAMPLES

The worksheet shown in FIG. 10A contains data taken for an aggregate sample of Chat Sand. The raw data is used to calculate apparent specific gravity and %absorption. A correction of 0.35% is applied to the calculated %abs of equation (7). The 0.35 correction can be determined by using the y intercept of the graph of FIG. 9A or by calculating the total absorption at maximum vacuum and selecting the corresponding correction from the graph in FIG. 9B.

As shown, various weights of the two samples are obtained and input into a data chart (which can be a computer-generated spreadsheet or various input screens on a computer display to allow a user to enter the data and the computer to generate the desired calculations). Columns 1–3 and 7 are used for the unsealed sample: Col. 1 is used to record the weight of the (dry) aggregate sample in an unsealed bag; Col. 2 is used to record the weight of the bag alone; and Col. 3 is used to record the weight of the aggregate and bag in the liquid bath. Columns 4–6 and 8 are used for the vacuum-sealed sample. Column 8 uses the results of Cols. 4–6 to determine the density of the sample. Column 4 is used to record the weight of the sample in the sealed bag, Col. 5 is for the bag weight alone, and Col. 6 is for the weight of the sealed bag and aggregate after the bag is opened and as they are held under water. Column 7 uses the results of Cols. 1–3 to determine the density of the other sample. Column 9 uses the data from both of the samples to calculate the percent absorption (and apply a 0.35% correction factor for the material undergoing analysis. Column 10 records the determined mass of the saturated sample in water (C); Col. 11 records the mass of the SSD sample in air (B); Cols. 12 and 13 illustrate that that the bulk specific gravity (dry basis) and the bulk specific gravity SSD can also be determined based on the values obtained by the methods and systems of the present invention.

The 0.891 value shown in FIG. 10A under the bag weight calculation, is a bag apparent density correction value (or other correction value for other containers as needed) and can be provided by an OEM or calculated as noted in co-pending and co-assigned U.S. patent application Ser. No. 09/580,792 the contents of which were incorporated by reference above.

FIG. 10B illustrates a different worksheet used to evaluate South Mississippi sand. The raw data can be used to calculate apparent density and % absorption. Columns 2–3 are for Sample A (the non-evacuated/sealed sample): Col. 2 for the dry sample weight in air and Col. 3, for the sample weight in the container filled with water. Column 4 is used to record the weight of the bag. Column 5 is used to record the weight of the dry sample B in air and Col. 6 is used to record the weight of the aggregate and bag in the liquid bath (opened). The absorption (porosity or other parameter) can be determined by using the recorded results. Of course, the data can be directly input from the scales or from an operator into a computer for digital calculation.

In summary, the methods and systems of the present invention can bypass direct determination of the mass at SSD (B value) that is typically difficult to define with fine aggregates. In addition, the absorption and/or specific gravity results are repeatable and less prone to operator variability than conventional procedures. Further, the determinations of calibration for absorption correction can be based on each specific material used and not restricted to a factor associated with a general or an average relationship. The test methodology of the proposed methods reduce the time required to perform this test down to approximately 5–30 minutes, and a twenty-four hour saturation is not required. Advantageously, this method can be used with coarse and fine aggregates as well as with high and low porosity materials.

The methods of embodiments of the invention can be suitable for analysis of loose and compacted materials including synthetic and natural aggregate materials such as, but not limited to, sand, silica, glass, limestone, chat sand, LA #30, MM, bulk or loose asphalt, concrete cylinders or specimens, or other loose, bulk, or compacted or uncompacted materials or shaped or formed specimens. The materials or specimens can comprise non-absorptive (such as glass) and/or absorptive materials (whether the material composition exhibits high, low, or intermediate absorption characteristics or porosity). Examples of some aggregates include blast furnace slag, synthetic and manufactured aggregates, and lightweight aggregates such as low-density materials (which may be used in concrete structures such as high-rise buildings).

Methods for determining absorption and/or specific gravity or other properties and characteristics according to embodiments of the present invention can be suitable for aggregate mixtures used in the preparation of concrete, paved asphalts, and concrete asphalts. In addition, the methods of the instant invention can be used to analyze aggregates taken on geological surveys or oil explorations. It is expected that confirmation of the degree or relative absorption or porosity of the aggregate or soil or other materials obtained during the surveys or explorations can provide valuable information on whether the site is likely to include oil or the desirable building or construction substructure. For example, a finding of higher absorption values may indicate that the site is worthy of additional or a more in-depth analysis.

It will be understood that each block of the flowchart illustration, and combinations of blocks in the flowchart illustrations as well as calculations, equations, data look-up charts, data manipulations, and calibration factor offset determinations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to allow user input (or automatic weight entry relayed by integrated scales) of data and to produce computer implemented process such that the instructions which execute on the computer or other programmable apparatus provide steps for implementing the functions specified in the flowchart block or blocks.

Accordingly, blocks of the flowchart illustrations and the numerical and mathematical relationships presented herein support combinations of means for performing the specified functions and program instruction means for performing the specified functions. It will also be understood that each block of the flowchart illustrations, and combinations of blocks in the flowchart illustrations, as well as calculations and determinations can be implemented by special purpose hardware-based computer systems which perform the specified functions or steps, or combinations of special purpose hardware and computer instructions. The blocks can be carried out in the order noted or in other orders. The operations described in the blocks can be combined or even separated into distinct operational segments. The computer systems and/or hardware can be integrated into a vacuum system or to operate with a computer associated with a vacuum system.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, when used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for analyzing material properties of a material sample comprising aggregate:
    obtaining a first aggregate material sample of a material undergoing analysis;
    drying the first aggregate material sample;
    determining the dry weight of the first aggregate material sample;
    providing a volumetric container, the volumetric container having a lid that attaches thereto that are configured together to be able to define a fixed or constant internal volume;
    partially filling the volumetric container with liquid;
    placing the first aggregate material sample in the volumetric container;
    adding additional liquid to the container after the first aggregate material is placed in the volumetric container;
    attaching the lid onto the volumetric container to enclose the liquid and aggregate material therein;
    measuring the weight of the volumetric container holding the first aggregate material sample and the liquid after the steps of attaching the lid and adding additional liquid;
    obtaining a second aggregate material sample of a material undergoing analysis;
    drying the second aggregate material sample;
    encasing the second aggregate sample in a vacuum-sealed second container;
    immersing the second aggregate material sample while it is held in the vacuum-sealed container in a liquid bath;
    opening the vacuum-sealed container as it is held immersed in the liquid bath;
    measuring the weight of the second aggregate material sample in the second opened container while they are held immersed in the liquid bath; and
    determining at least one of the percent absorption, apparent specific gravity, bulk specific gravity, and saturated surface dry (SSD) weight of the aggregate undergoing analysis based on the weights obtained in said measuring steps.

2. A method according to claim 1, wherein the first and second aggregate samples are different samples partitioned from a single larger aggregate material sample.

3. A method according to claim 1, wherein the first and second aggregate material samples are the same sample.

4. A method according to claim 1, wherein the first and second material samples comprises fine aggregate.

5. A method according to claim 4, wherein the step of adding another quantity of liquid through the lid comprises:
    inserting a syringe having a liquid delivery lumen and holding a quantity of liquid therein through the port in the lid such that the end of the lumen resides below the liquid level in the volumetric container; and
    expelling liquid from the syringe such that it enters the container under the surface of the liquid level in an amount sufficient to fill the internal volume of the volumetric container and lid.

6. A method according to claim 5, further comprising positioning the volumetric container on a fixture having a holding platform and a plurality of clamps thereon, the holding platform being sized and configured to hold the volumetric container thereon during the steps of attaching the lid and measuring the weight of the volumetric container and liquid and aggregate sample, and wherein the step of attaching comprises positioning and extending the clamps to exert downward forces on to the lid so as to seal the volumetric container and lid together.

7. A method according to claim 1, wherein the first and second material samples substantially comprises only fine or very fine aggregates.

8. A method according to claim 1, wherein the second container is a collapsible bag.

9. A method according to claim 1, wherein the lid of the volumetric container comprises a liquid entry port, and wherein the step of adding additional liquid comprises:

adding a first amount of additional liquid to a level that is below the top of the volumetric container; and after the step of attaching the lid, adding a second amount of liquid into the volumetric container through the liquid entry port so that the liquid with the aggregate fills the container and occupies the fixed internal volume.

10. A method according to claim 1, further comprising filling the enclosed container with liquid alone and obtaining a weight thereof to obtain a calibration weight of the volumetric container with a lid.

11. A method according to claim 10, further comprising distributing or dislodging the aggregate sample across the bottom of the volumetric container before the step of adding additional liquid.

12. A method according to claim 11, wherein the material sample comprises coarse aggregate, and wherein the container comprises a nested inner bag and an outer bag, the outer bag being configured to be vacuum-sealed about the second material sample.

13. A method according to claim 1, wherein the first and second material aggregate samples comprise coarse aggregate, and wherein the step of adding additional liquid comprises adding additional liquid to a predetermined level such that the liquid level is substantially at the top of the volumetric container before the step of attaching the lid, and wherein the step of attaching the lid forces liquid from the volumetric container and encloses the internal volume so that the liquid and aggregate fill and occupy the internal fixed volume.

14. A method according to claim 1, wherein the container comprises at least one collapsible bag, and wherein the step of opening the bag comprises introducing a first opening on a first upper edge portion of the bag, then allowing liquid to enter into the bag, and then introducing a second opening into a second upper edge portion on an opposing side of the bag.

15. A method according to claim 1, wherein the steps of placing, adding additional liquid, attaching the lid, and measuring the weight of the volumetric container holding the first aggregate material sample and the liquid are carried out in less than about 3 minutes.

16. A method according to claim 15, wherein the recited steps are carried out in about two minutes or less.

17. A system for analyzing material properties of a material sample comprising aggregate:

means for obtaining a first aggregate material sample of a material undergoing analysis;

means for doing the fiat aggregate material sample;

means for determining the dry weight of the first aggregate material sample means for providing a volumetric container, the volumetric container having a lid that attaches thereto chat are configured together to be able so define a fixed at constant internal volume;

means for partially filling the volumetric container with liquid;

means for placing the first aggregate material sample in the volumetric container means for adding additional liquid to the container alter the tint aggregate material is placed in the volumetric container;

means for attaching the lid onto the volumetric container to enclose the liquid and aggregate material therein;

means for measuring the weigh; of she volumetric container holding the first aggregate material sample and the liquid after the step of attaching the lid and adding additional liquid;

means for obtaining a second aggregate material sample of a material undergoing analysis;

means for drying the second aggregate material sample;

means for encasing the second aggregate sample in a vacuum-sealed second container means for immersing the second aggregate, material sample while it is held in the vacuum-sealed container its a liquid bath;

means for opening the vacuum-sealed container as it is held immersed in the liquid bath;

means for measuring the weight of the second aggregate material sample in the second opened container while they are held immersed in the liquid bath; and means for determining at least cue of the percent absorption, apparent specific gravity, bulk specific gravity, and saturated surface dry (SSD) weight of the aggregate undergoing analysis based on the weights obtained.

* * * * *

UNITED STATES PATENT AND TRADEMARK OFFICE
CERTIFICATE OF CORRECTION

PATENT NO. : 6,817,230 B2
APPLICATION NO. : 10/462499
DATED : November 16, 2004
INVENTOR(S) : James et al.

It is certified that error appears in the above-identified patent and that said Letters Patent is hereby corrected as shown below:

Column 36

Line 15 should read -- means for drying the first aggregate material sample; --

Line 17 should read -- gate material sample; means for providing a volumetric --

Lines 19-20 should read -- attaches thereto that are configured together to be able to define a fixed or constant internal volume; --

Lines 24-25 should read -- the volumetric container; means for adding additional liquid to the container after the first aggregate material --

Line 30 should read -- means for measuring the weight of the volumetric container --

Line 32 should read -- the liquid after the steps of attaching the lid and adding --

Lines 39-41 should read -- vacuum-sealed second container; means for immersing the second aggregate material sample while it is held in the vacuum-sealed container in a liquid bath; --

Line 47 should read -- means for determining at least one of the percent --

Signed and Sealed this

Twenty-fifth Day of December, 2007

JON W. DUDAS
*Director of the United States Patent and Trademark Office*